(12) United States Patent
Shimomura et al.

(10) Patent No.: US 8,282,725 B2
(45) Date of Patent: Oct. 9, 2012

(54) SELF-DISPERSION PIGMENT, PRODUCTION PROCESS OF SELF-DISPERSION PIGMENT, INK SET AND INK JET RECORDING METHOD

(75) Inventors: Naofumi Shimomura, Kawasaki (JP); Ai Shinohara, Tokyo (JP); Eri Watanabe, Kawasaki (JP); Yutaka Kurabayashi, Higashimurayama (JP)

(73) Assignee: Canon Kabushiki Kaisha, Tokyo (JP)

( * ) Notice: Subject to any disclaimer, the term of this patent is extended or adjusted under 35 U.S.C. 154(b) by 339 days.

(21) Appl. No.: 12/757,513

(22) Filed: Apr. 9, 2010

(65) Prior Publication Data

US 2010/0271418 A1 Oct. 28, 2010

(30) Foreign Application Priority Data

Apr. 22, 2009 (JP) ................................. 2009-104215

(51) Int. Cl.
*C09D 11/00* (2006.01)
(52) U.S. Cl. ..................................................... 106/31.6
(58) Field of Classification Search .................. 106/31.6
See application file for complete search history.

(56) References Cited

U.S. PATENT DOCUMENTS

| | | | |
|---|---|---|---|
| 5,081,470 A | 1/1992 | Kurabayashi et al. | |
| 5,124,201 A | 6/1992 | Kurabayashi et al. | |
| 5,137,778 A | 8/1992 | Nakatsugawa et al. | |
| 5,171,626 A | 12/1992 | Nagamine et al. | |
| 5,246,774 A | 9/1993 | Sakaki et al. | |
| 5,277,962 A | 1/1994 | Nakatsugawa et al. | |
| 5,362,558 A | 11/1994 | Sakaki et al. | |
| 5,415,686 A | 5/1995 | Kurabayashi et al. | |
| 5,439,515 A | 8/1995 | Kurabayashi et al. | |
| 5,526,031 A | 6/1996 | Kurabayashi | |
| 5,549,740 A | 8/1996 | Takahashi et al. | |
| 5,614,007 A | 3/1997 | Kurabayashi et al. | |
| 5,618,338 A | 4/1997 | Kurabayashi et al. | |
| 5,623,294 A | 4/1997 | Takizawa et al. | |
| 5,624,484 A | 4/1997 | Takahashi et al. | |
| 5,651,814 A | 7/1997 | Shimomura et al. | |
| 5,700,314 A | 12/1997 | Kurbayashi et al. | |
| 5,707,432 A | 1/1998 | Adams et al. | |
| 5,734,403 A | 3/1998 | Suga et al. | |
| 5,792,249 A | 8/1998 | Shirota et al. | |
| 5,835,116 A | 11/1998 | Sato et al. | |
| 5,849,815 A | 12/1998 | Aoki et al. | |
| 5,985,975 A | 11/1999 | Kurabayashi et al. | |
| 6,027,210 A | 2/2000 | Kurabayashi et al. | |
| 6,238,045 B1 | 5/2001 | Ono et al. | |
| 6,322,209 B1 | 11/2001 | Sato et al. | |
| 6,341,855 B1 | 1/2002 | Kurabayashi | |
| 6,342,096 B1 | 1/2002 | Kurabayashi | |
| 6,367,921 B1 | 4/2002 | Kurabayashi et al. | |
| 6,398,355 B1 | 6/2002 | Shirota et al. | |
| 6,399,674 B1 | 6/2002 | Kashiwazaki et al. | |
| 6,412,936 B1 | 7/2002 | Mafune et al. | |
| 6,460,989 B1 | 10/2002 | Yano et al. | |
| 6,471,757 B1 | 10/2002 | Koitabashi et al. | |
| 6,517,199 B1 | 2/2003 | Tomioka et al. | |
| 6,521,323 B1 | 2/2003 | Sakaki et al. | |
| 6,536,890 B1 | 3/2003 | Kato et al. | |
| 6,719,420 B2 | 4/2004 | Tomioka et al. | |
| 6,746,114 B2 | 6/2004 | Takahashi et al. | |
| 6,780,901 B1 | 8/2004 | Endo et al. | |
| 6,790,878 B2 | 9/2004 | Kurabayashi | |
| 6,794,427 B2 | 9/2004 | Kurabayashi et al. | |
| 6,821,328 B2 | 11/2004 | Tomioka et al. | |
| 6,966,944 B2 | 11/2005 | Shimomura et al. | |
| 7,198,837 B1 | 4/2007 | Endo et al. | |
| 7,208,032 B2 | 4/2007 | Hakamada et al. | |
| 7,285,310 B2 | 10/2007 | Kanke et al. | |
| 7,297,194 B2 | 11/2007 | Shinjo et al. | |
| 7,503,649 B2 | 3/2009 | Kishi et al. | |
| 7,517,073 B2 | 4/2009 | Nito et al. | |
| 7,517,074 B2 | 4/2009 | Hakamada et al. | |
| 2006/0098067 A1* | 5/2006 | Imai et al. ..................... 347/100 |
| 2009/0136680 A1 | 5/2009 | Kishi et al. | |
| 2010/0269732 A1* | 10/2010 | Sekiyama .................... 106/31.9 |

FOREIGN PATENT DOCUMENTS

| | | | |
|---|---|---|---|
| JP | 8-003498 A | | 1/1996 |
| JP | 2005255705 A | * | 9/2005 |
| JP | 4001922 B2 | | 10/2007 |
| WO | WO 2009084714 A1 | * | 7/2009 |

OTHER PUBLICATIONS

Machine Translation of JP 2005-255705.*

* cited by examiner

*Primary Examiner* — Melvin C Mayes
*Assistant Examiner* — Veronica F Faison
(74) *Attorney, Agent, or Firm* — Fitzpatrick, Cella, Harper & Scinto

(57) ABSTRACT

The invention provides a self-dispersion pigment including a pigment, an ionic group directly bonded to the pigment and a nonionic molecular chain bonded to the pigment through an amide bond.

14 Claims, No Drawings

SELF-DISPERSION PIGMENT, PRODUCTION PROCESS OF SELF-DISPERSION PIGMENT, INK SET AND INK JET RECORDING METHOD

BACKGROUND OF THE INVENTION

1. Field of the Invention

The present invention relates to a self-dispersion pigment excellent in dispersion stability in an aqueous medium, a production process thereof, an ink set and an ink jet recording method.

2. Description of the Related Art

In recent years, attention has been paid to pigments excellent in light resistance and water resistance compared with dyes as coloring materials for aqueous inks used in ink jet recording. However, since a pigment is insoluble in water, the pigment needs to be stably present in water for using it as a coloring material of an aqueous ink. Treatment techniques for pigments for stably dispersing a pigment in an aqueous medium have recently come to be actively developed. Among these techniques developed, such a technique of making a pigment self-dispersible that pigment itself is treated to improve the dispersibility of the pigment itself, thereby making it a self-dispersion pigment dispersible in an aqueous medium without using any dispersant is particularly favorably used as techniques for treating pigments for ink jet aqueous inks, because reliability with respect to an ink jet head is high.

As one of the above-described techniques for treating the pigment itself, Japanese Patent Application Laid-Open No. H08-3498 describes a technique for oxidatively treating a pigment with an oxidizing agent. Japanese Patent No. 4001922 describes a technique for treating a pigment with a diazonium salt.

SUMMARY OF THE INVENTION

However, the present inventors have carried out an investigation as to the technique of Japanese Patent Application Laid-Open No. H08-3498. As a result, dispersion stability has been unable to be imparted to a pigment to more than a certain extent even when the amount of the oxidizing agent added or the number of times of the oxidation treatment has been increased. A self-dispersion pigment produced by using the technique of Japanese Patent No. 4001922 permeates into the interior of a recording medium upon printing to fail to achieve a sufficient image density though good dispersion stability has been achieved. When a color image has been formed, color bleed (hereinafter also referred to as "bleeding") has occurred at boundary portions between inks different in color tone, resulting in a failure to obtain an image of a satisfactory level to the present inventors.

It is an object of the present invention to provide a self-dispersion pigment having extremely high dispersion stability in an aqueous medium and a production process of the self-dispersion pigment. Another object of the present invention is to provide an ink set of an ink jet aqueous ink and a liquid composition, by which an image having an excellent image density and reduced in bleeding is provided, and an ink jet recording method using the ink set.

The present invention provides a self-dispersion pigment including a pigment, an ionic group directly bonded to the pigment and a nonionic molecular chain bonded to the pigment through an amide bond.

The present invention also provides a production process of the self-dispersion pigment, an ink set of an ink containing the self-dispersion pigment and a liquid composition, and an ink jet recording method using the ink set.

According to the present invention, there can be provided a self-dispersion pigment excellent in dispersion stability in an aqueous medium and a production process of the self-dispersion pigment. There can also be provided an ink set of an ink jet aqueous ink and a liquid composition, by which an image having an excellent image density and reduced bleeding is realized, and an ink jet recording method using the ink set.

Further features of the present invention will become apparent from the following description of exemplary embodiments.

DESCRIPTION OF THE EMBODIMENTS

Preferred embodiments of the present invention will now be described in detail.

<Self-Dispersion Pigment>

The self-dispersion pigment according to the present invention has at least a pigment, an ionic group directly bonded to the pigment and a nonionic molecular chain bonded to the pigment through an amide bond. The respective components of the self-dispersion pigment according to the present invention will hereinafter be described in detail.

[Pigment]

In the present invention, any of a black pigment and a color pigment may be used. Specifically, the following pigments may be favorably used.

Examples of the black pigment include carbon black pigments such as furnace black, lamp black, acetylene black and channel black. Among the carbon black pigments described above, carbon black having a primary particle size of 5 nm or more and 40 nm or less, a specific surface area of 40 $m^2/g$ or more and 600 $m^2/g$ or less as determined according to the BET method, and a pH value of 2 or more and 10 or less is favorable. In the present invention, the primary particle size may be calculated in the following manner using an electron microscope such as SEM. In the case of using SEM, after an SEM image is photographed, about 30 to 50 pigment particles are arbitrarily picked up from the image photographed, and the diameter of each of the pigment particles picked up is measured to calculate the diameter of the pigment particle in view of the scale. The average value of the diameters of the respective pigment particles calculated is determined, whereby the primary particle size of the pigment can be calculated.

Specific examples of the carbon black having the above-described primary particle size and specific surface area include No.: 33, 40, 45, 52, 900, 2200B and 2300, MA7, MA8, and MCF88 (all, products of MITSUBISHI CHEMICAL CORPORATION); RAVEN 1255 (product of Columbian Carbon Co.); REGAL: 300R, 400R and 660R, and MOGUL L (all, products of CABOT CO.); and Nipex 160IQ, Nipex 170IQ, Nipex 75, Printex 95, Printex 90, Printex 80, Printex 85, Printex 35 and Printex U (all, products of Degussa AG).

Color pigments usable in the present invention include the following pigments. Examples of yellow pigments include C.I. Pigment Yellow: 1, 2, 3, 13, 16, 74, 83, 109, 128 and 155. Examples of magenta pigments include C.I. Pigment Red: 5, 7, 12, 48(Ca), 48(Mn), 57(Ca), 57:1, 112 and 122, quinacridone solid solution, and C.I. Pigment Violet 19. Examples of cyan pigments include C.I. Pigment Blue: 1, 2, 3, 15:3, 15:4, 16 and 22, and C.I. Vat Blue: 4 and 6.

Needless to say, the pigments are not limited to these pigments in the present invention, and other color pigments than the above-described color pigments may also be used.

Two or more pigments may be mixed for use. In addition, newly prepared pigments may also be used.

<Ionic Group Directly Bonded to Pigment>

In the present invention, no particular limitation is imposed on the ionic group directly bonded to the pigment, and any of an anionic group and a cationic group may be used. Since the ionic group is ionized in an aqueous medium and the ionized ionic group portions repulse each other due to electric charges to inhibit aggregation between self-dispersion pigment particles, the self-dispersion pigment having the ionic group directly bonded to the pigment is dispersible in an aqueous medium. Incidentally, "ionic group directly bonded to pigment" means a functional group which is bonded to the pigment through no other atomic group and exhibits ionicity.

The ionic group directly bonded to the pigment is favorably an anionic group. The anionic group has relatively less limitations in terms of chemical safety compared with a cationic group, so that various functional groups can be selected.

[Anionic Group]

Specific examples of the anionic group directly bonded to the pigment in the present invention include —COO(M), —SO$_3$(M) and —PO$_3$H(M). Incidentally, M is a hydrogen atom, alkali metal, ammonium or organic ammonium. However, the anionic group is not limited to the above-described groups in the present invention, and any other anionic group than that described above may be directly bonded to the pigment. Among the anionic groups directly bonded to the pigment, —COO(M) is favorable because it can impart high dispersion stability to the pigment compared with —SO$_3$(M) and is cheaper than —PO$_3$H(M). It is not necessary that only one kind of anionic group is directly bonded to the pigment, but plural kinds of anionic groups may be added to the pigment. Incidentally, since the anionic group is present being ionized in an ink, for example, —COO(M) may take a state of —COO$^-$ in the ink. In the present invention, all anionic groups in Examples, which will be described subsequently, are expressed in the form of a salt for the sake of brevity of description.

<Nonionic Molecular Chain Bonded to Pigment Through Amide Bond>

The self-dispersion pigment according to the present invention has a nonionic molecular chain bonded to the pigment through an amide bond. In the present invention, "nonionic molecular chain" means a molecular chain having at least one carbon atom all functional groups of which are nonionic groups. In the present invention, the case where a nonionic group is a nonionic molecular chain, to be specific, a nonionic group such as —CH$_3$, may also be called a nonionic molecular chain. The self-dispersion pigment has the nonionic molecular chain bonded to the pigment through the amide bond, whereby the self-dispersion pigment can retain high dispersion stability even when the pigment is stored for a long period of time. The present inventors infer the reason why the above effect is developed as follows. Since the nonionic molecular chain is bonded to the pigment through the amide bond, this molecular chain has high steric hindrance. Therefore, steric repulsion acts between pigment particles to inhibit association between pigment particles. In addition, the amide bond is hard to be hydrolyzed compared with an ester bond, so that the amide bond can firmly bond the pigment to the nonionic molecular chain. Accordingly, detachment of the nonionic molecular chain during long-term storage can be reduced to provide a self-dispersion pigment excellent in dispersion stability during long-term storage.

The nitrogen atom forming the amide bond in the present invention is favorably tertiary. When the nitrogen atom is tertiary, two nonionic molecular chains can be bonded to one amide bond. Therefore, the tertiary nitrogen atom can impart high steric repulsion compared with a secondary nitrogen atom, by which one nonionic molecular chain is bonded to one amide bond.

It is favorable that the nonionic molecular chain is of hydrocarbon, and the hydrocarbon has a cyclic hydrocarbon. The nonionic molecular chain has the hydrocarbon, whereby high steric hindrance can be achieved to inhibit association between pigment particles. Likewise, it is favorable that the nonionic molecular chain is of hydrocarbon, and at least one carbon atom of the carbon atoms of the hydrocarbon is a quaternary carbon atom. The quaternary carbon atom is directly bonded to 4 carbon atoms. Therefore, high steric hindrance compared with a straight chain hydrocarbon can be achieved.

The nonionic molecular chain favorably contains an alkyl ether. Since the alkyl ether is hydrophilic, the affinity of the self-dispersion pigment for water can be improved. Therefore, the self-dispersion pigment containing the alkyl ether can stably be present in water. The nonionic molecular chain containing the alkyl ether is favorably a polymer chain. The weight-average molecular weight of the alkyl ether is favorably 500 or more and 10,000 or less. The weight-average molecular weight of the alkyl ether means a weight-average molecular weight in terms of polyethylene glycol as measured by GPC.

The structure of the nonionic molecular chain according to the present invention can be identified by the following method. An excessive amount of an aqueous solution of sodium hydroxide or an aqueous solution of hydrochloric acid is added to a self-dispersion pigment dispersion liquid containing the self-dispersion pigment, and the resultant mixture is stirred under hydrolysis conditions of the amide bond. After stirring, the self-dispersion pigment is precipitated by a centrifugal separator to collect the supernatant liquid. The aqueous medium in the supernatant liquid collected was evaporated to collect solids. The solids collected are analyzed by NMR, IR and elemental analysis, whereby the structure of the nonionic molecular chain can be identified.

<Amounts of Ionic Group and Nonionic Molecular Chain Per Unit Mass of Pigment>

It is generally known to use mmol/g as unit indicating the amount of a functional group or molecular chain per unit mass of a pigment. In the present invention, the amount of the ionic group per unit mass of the pigment in the self-dispersion pigment or the amount of the nonionic molecular chain per said unit mass will hereinafter be described in detail. In the description, "the amount of the ionic group per unit mass of the pigment in the self-dispersion pigment" may hereinafter be also referred to as "the amount of the ionic group" merely, and "the amount of the nonionic molecular chain per unit mass of the pigment in the self-dispersion pigment" may be also referred to as "the amount of the nonionic molecular chain" merely.

In the self-dispersion pigment according to the present invention, the total amount of the ionic group and nonionic molecular chain is favorably 0.20 mmol/g or more. When the total amount is 0.20 mmol/g or more, the self-dispersion pigment can achieve high dispersion stability. The total amount is more favorably 0.35 mmol/g or more, particularly favorably 0.50 mmol/g or more.

The total amount is favorably 2.0 mmol/g or less. When the total amount is 2.0 mmol/g or less, the pigment is easy to aggregate on a recording medium, and lowering of an image density and occurrence of bleeding can be more inhibited, so that a printed article having far excellent image properties can be obtained. Incidentally, in the case of an ink set of an ink containing the self-dispersion pigment according to the present invention and a liquid composition which will be described subsequently, no particular limitation is imposed on the upper limit of the above-described total amount. Since the self-dispersion pigment in the ink and the component in the liquid composition for aggregating coloring materials rapidly aggregate, the lowering of the image density and the occurrence of bleeding are more inhibited than the case of singly using the ink containing the self-dispersion pigment. If the upper limit is mentioned, the total amount in the ink set of the ink and the liquid composition is favorably 3.0 mmol/g or less.

The total amount of the ionic group and nonionic molecular chain in the present invention can be measured by the following method. An excessive amount of an aqueous solution of sodium hydroxide or an aqueous solution of hydrochloric acid is added to a self-dispersion pigment dispersion liquid containing the self-dispersion pigment, and the resultant mixture is stirred under hydrolysis conditions of the amide bond. After stirring, the self-dispersion pigment is precipitated by a centrifugal separator to collect the self-dispersion pigment precipitated. After the self-dispersion pigment is dehydrated, dried and then weighed, a known amount of sodium hydrogencarbonate is added, and the resultant mixture is stirred. After stirring, the self-dispersion pigment is precipitated by a centrifugal separator to collect a supernatant liquid. The supernatant liquid collected is weighed to conduct neutralization titration with a known amount of hydrochloric acid, thereby calculating the total amount of the ionic group and nonionic molecular chain from the titer.

The proportion of the amount of the ionic group per unit mass of the pigment in the self-dispersion pigment to the total amount of the amount of the ionic group per unit mass of the pigment and the amount of the nonionic molecular chain per unit mass of the pigment is favorably 5.0% or more. When the proportion is 5.0% or more, the ink containing the self-dispersion pigment can have good fixability when the ink is used as an ink set with a liquid composition containing a component for aggregating a coloring material. The proportion is more favorably 10.0% or more, still more favorably 15.0% or more. The proportion of the amount of the ionic group per unit mass of the pigment in the self-dispersion pigment to the total amount of the amount of the ionic group per unit mass of the pigment and the amount of the nonionic molecular chain per unit mass of the pigment is favorably 99.5% or less, more favorably 95% or less.

In the present invention, the amount of the ionic group per unit mass of the pigment in the self-dispersion pigment can be measured by the following method. An excessive amount of an aqueous solution of hydrochloric acid is added to a self-dispersion pigment dispersion liquid containing the self-dispersion pigment, and the resultant mixture is stirred. After stirring, the self-dispersion pigment is precipitated by a centrifugal separator, and the self-dispersion pigment precipitated is collected. After the self-dispersion pigment is dehydrated, dried and then weighed, a known amount of sodium hydrogencarbonate is added, and the resultant mixture is stirred. After stirring, the self-dispersion pigment is precipitated by a centrifugal separator to collect a supernatant liquid. The supernatant liquid collected is weighed to conduct neutralization titration with a known amount of hydrochloric acid, thereby calculating the amount of the ionic group from the titer.

The amount of the nonionic molecular chain per unit mass of the pigment in the self-dispersion pigment according to the present invention is favorably 0.010 mmol/g or more. If the amount is less than 0.010 mmol/g, the steric repulsion of the self-dispersion pigment by the nonionic molecular chain is not sufficiently achieved, and so the dispersion stability may be lowered in some cases. The amount of the nonionic molecular chain per unit mass of the pigment is more favorably 0.050 mmol/g or more, particularly favorably 0.100 mmol/g or more. The amount of the nonionic molecular chain per unit mass of the pigment in the self-dispersion pigment according to the present invention is favorably 1.9 mmol/g or less, more favorably 1.7 mmol/g or less. The amount of the nonionic molecular chain in the present invention can be calculated by subtracting the amount of the ionic group from the total amount of the ionic group and nonionic molecular chain.

<Ink Jet Aqueous Ink>

The ink jet aqueous ink (also referred to as "ink" merely) according to the present invention is only required to contain the self-dispersion pigment according to the present invention and an aqueous medium. No particular limitation is imposed on the content of the self-dispersion pigment in the ink jet aqueous ink. However, the content is favorably 1% by mass or more and 20% by mass or less based on the total mass of the ink jet aqueous ink.

[Aqueous Medium]

The ink jet aqueous ink according to the present invention contains an aqueous medium. Examples of the aqueous medium include water or a mixed solvent of water and a water-soluble organic solvent. Deionized water is favorably used as the water in the present invention. Examples of the water-soluble organic solvent used in the present invention include alkyl alcohols having 1 to 4 carbon atoms, such as methyl alcohol, ethyl alcohol, n-propyl alcohol, isopropyl alcohol, n-butyl alcohol, sec-butyl alcohol and tert-butyl alcohol; amides such as dimethylformamide and dimethylacetamide; ketones and ketone alcohols such as acetone and diacetone alcohol; ethers such as tetrahydrofuran and dioxane; polyalkylene glycols such as polyethylene glycol and polypropylene glycol; alkylene glycols the alkylene group of which has 2 to 6 carbon atoms, such as ethylene glycol, propylene glycol, butylene glycol, triethylene glycol, 1,2,6-hexanetriol, thiodiglycol, hexylene glycol and diethylene glycol; lower alkyl ether acetates such as polyethylene glycol monomethyl ether acetate; glycerol; lower alkyl ethers of polyhydric alcohols, such as ethylene glycol monomethyl (or ethyl)ether, diethylene glycol methyl (or ethyl)ether and triethylene glycol monomethyl (or ethyl)ether; polyhydric alcohols such as trimethylolpropane and trimethylolethane; N-methyl-2-pyrrolidone; 2-pyrrolidone; and 1,3-dimethyl-2-imidazolidinone. The water-soluble organic solvents may be used either singly or in any combination thereof. No particular limitation is imposed on the content of the aqueous medium in the ink jet aqueous ink. However, the content is favorably 50% by mass or more and 95% by mass or less based on the total mass of the ink jet aqueous ink. The content of the water-soluble organic solvent in the ink jet aqueous ink is favorably 3% by mass or more and 50% by mass or less based on the total mass of the ink jet aqueous ink. The ink jet aqueous ink according to the present invention may contain a surfactant. Specific examples of the surfactant include Acetylenol 100 (product of Kawaken Fine Chemicals Co., Ltd.), Acetylenol 40 (product of Kawaken Fine Chemicals Co., Ltd.), BC-20 (product of Nikko Chemicals Co., Ltd.) and L31 (product of ADEKA CORPORATION). The content of the surfactant is favorably 0.1% by mass or more and 2.0% by mass or less based on the total mass of the ink.

Besides the above components, additives such as a pH adjustor, a preservative and a water-soluble resin may be suitably added to the ink jet aqueous ink according to the present invention as needed. As the pH adjustor and preservative, may be used those generally used. No particular limitation is imposed on the water-soluble resin. However, polyvinyl alcohol or polyvinyl pyrrolidone may be used.

<Ink Set>

The ink jet aqueous ink according to the present invention can achieve high effect even when it is singly used. However, the ink jet aqueous ink is favorably used as an ink set with a liquid composition containing a component for aggregating the self-dispersion pigment in the ink jet aqueous ink. The component for aggregating the self-dispersion pigment in the liquid composition aggregates the self-dispersion pigment in the ink, whereby the fixability can be improved, and the occurrence of bleeding can be reduced. The investigation by the present inventors has revealed that the self-dispersion pigment with the ionic group directly bonded to the pigment has high reactivity compared with a self-dispersion pigment with the ionic group bonded to the pigment through another atomic group.

<Liquid Composition>

The liquid composition according to the present invention has at least a component for aggregating the self-dispersion pigment. The liquid composition is favorably transparent. However, the liquid composition is not always required not to exhibit absorption in a visible region. In other words, the liquid composition may exhibit absorption in the visible region so far as an image is not substantially affected by absorption in the visible region. Specifically, when the absorbance is 0.1 or less in a wavelength range of from 400 nm to 700 nm when the visible light absorption spectrum of the liquid composition is measured, the image is not substantially affected.

[Component for Aggregating Self-Dispersion Pigment]

In the self-dispersion pigment according to the present invention, the ionic group is directly bonded to the pigment. Therefore, since electrostatic repulsion between self-dispersion pigment particles is lost when the electric charge of the ionic group is removed, the aggregating ability of the self-dispersion pigment is improved. In order to utilize the above-described property of the self-dispersion pigment according to the present invention, the component for aggregating the self-dispersion pigment has, in water, an electric charge of a polarity opposite to that of the ionic group of the self-dispersion pigment. Therefore, when the ionic group is an anionic group, the component for aggregating the self-dispersion pigment exhibits cationicity in water.

Specific examples of the component for aggregating the self-dispersion pigment when the ionic group is an anionic group include metal salts, cationic polymers and pH buffering agents. Specific examples of the component for aggregating the self-dispersion pigment when the ionic group is a cationic group include anionic polymers.

Metal Salt

In the present invention, the metal salt is composed of a metal ion and an anion. Specific examples of the metal ion include divalent metal ions such as $Ca^{2+}$, $Cu^{2+}$, $Ni^{2+}$, $Mg^{2+}$, $Zn^{2+}$, $Sr^{2+}$ and $Ba^{2+}$, and trivalent metal ions such as $Al^{3+}$, $Fe^{3+}$, $Cr^{3+}$ and $Y^{3+}$. Examples of the anion include $Cl^-$, $NO_3^-$, $I^-$, $Br^-$, $ClO_3^-$, $SO_4^{2-}$, $CO_3^{2-}$, $CH_3COO^-$ and $HCOO^-$.

In the present invention, $Ca^{2+}$, $Mg^{2+}$, $Sr^{2+}$, $Al^{3+}$ and $Y^{3+}$ are particularly favorable as the metal ion from the viewpoints of reactivity, colorability and easy handling, and $Ca^{2+}$ is favorably used. $NO_3^-$ is particularly favorable as the anion from the viewpoint of solubility. The content of the metal salt in the liquid composition is favorably 0.01% by mass or more and 20% by mass or less based on the total mass of the liquid composition.

Cationic Polymer

In the present invention, specific examples of the cationic polymer include polyallylamine, poly(amine sulfone) and copolymers thereof, and polyvinylamine. The weight-average molecular weight of the cationic polymer is favorably 400 or more and 5,000 or less. Incidentally, the weight-average molecular weight in the present invention means a weight-average molecular weight in terms of polyethylene glycol as measured by GPC. The content of the cationic polymer is favorably 1.0% by mass or more and 50.0% by mass or less based on the total mass of the liquid composition.

pH Buffering Agent

In the present invention, specific examples of the pH buffering agent include oxalic acid, malonic acid, succinic acid, glutaric acid, citric acid, gluconic acid, malic acid, piperidinic acid, glutamic acid, sulfamic acid, aminoformic acid, p-anisic acid, N-methylmorpholine and N-oxides. The content of the pH buffering agent in the liquid composition is favorably 0.01% by mass or more and 70% by mass or less based on the total mass of the liquid composition.

{Aqueous Medium in Liquid Composition}

Any of the aqueous media usable in the ink jet aqueous ink may be used in the liquid composition according to the present invention. The content of the aqueous medium in the liquid composition is favorably 25% by mass or more and 95% by mass or less based on the total mass of the liquid composition. The content of the water-soluble organic solvent in the liquid composition is favorably 3% by mass or more and 70% by mass or less based on the total mass of the liquid composition.

[Other Components in Liquid Composition]

Polyvinyl alcohol or polyvinyl pyrrolidone may be added to the liquid composition according to the present invention for more improving scratch resistance and highlighter resistance. A low-volatile solvent is favorably used in the aqueous medium for the purpose of improving ejection of the liquid composition. The liquid composition according to the present invention may also contain a surfactant. Specific examples of the surfactant include Acetylenol 100 (product of Kawaken Fine Chemicals Co., Ltd.), Acetylenol 40 (product of Kawaken Fine Chemicals Co., Ltd.), BC-20 (product of Nikko Chemicals Co., Ltd.) and L31 (product of ADEKA CORPORATION). The content of the surfactant is favorably 0.1% by mass or more and 2.0% by mass or less based on the total mass of the liquid composition.

<Production Process of Self-Dispersion Pigment>

No particular limitation is imposed on the production process of the self-dispersion pigment according to the present invention. However, when the ionic group directly bonded to the pigment is a carboxyl group or sulfonic group, the following process may be favorably used. The process is a process for causing a pigment to which a carboxyl group or sulfonic group has been directly bonded, a condensing agent and an amine compound, which will be described subsequently, to react with one another. By using this process, a self-dispersion pigment high in dispersion stability and excellent in image properties can be obtained at a high yield. The mechanism thereof will hereinafter be described taking the case where the ionic group is a carboxyl group as an example. The same shall apply to the case where the ionic group is a sulfonic group except that the amide bond is changed to a sulfonamide bond.

When the pigment, to which a carboxyl group has been directly bonded, the condensing agent and the amine compound are caused to react, the carboxyl group reacts with an amino group of the amine compound to form an amide bond. As a result, a self-dispersion pigment in which the pigment is bonded to another site than the amino group of the amine compound through the amide bond can be obtained. For example, when methylamine is used as the amine compound, a self-dispersion pigment in which the pigment is bonded to the methyl group through the amide bond can be obtained.

As described above, the carboxyl group becomes a site for forming the amide bond in the present invention, so that in the case where the ionic group is a carboxyl group, the total amount of the carboxyl group directly bonded to the finally resulting self-dispersion pigment and the amide bond directly bonded to the pigment is equal to the amount of the carboxyl group of the self-dispersion pigment prior to the step of forming the amide bond. Accordingly, a pigment in which the carboxyl group is excessively modified by the amount of the carboxyl group to be lost by the formation of the amide bond in advance is used, whereby a self-dispersion pigment containing the respective desired amounts of the carboxyl group and the amide bond can be obtained.

As the pigment to which the carboxyl group has been directly bonded, may be used any of the following commercially available oxidized pigments. Specific examples of usable pigments include Aqua-Black 001 (Tokai Carbon Co., Ltd.), Aqua-Black 162 (Tokai Carbon Co., Ltd.), BONJET BLACK CW-1 (Orient Chemical Industries Ltd.), BONJET BLACK CW-2 (Orient Chemical Industries Ltd.) and BONJET BLACK M-800 (Orient Chemical Industries Ltd.). The carboxyl group may be directly bonded to a pigment subjected to no surface treatment. As a method for directly bonding the carboxyl group to the pigment, is mentioned a method of oxidatively treating a pigment with an oxidizing agent such as sodium hypochlorite.

In the present invention, in the formation of the amide bond, it is required to add a condensing agent. By adding the condensing agent, the amide bond can be obtained at a high yield.

No particular limitation is imposed on the condensing agent usable in the present invention. However, the following condensing agents may be specifically used. Specific examples of condensing agents usable include acetic anhydride, 4-dimethylaminopyridine, N,N-dicyclohexylcarbodiimide, diphenylphosphorylazide, N,N-diisopropylcarbodiimide, 1,1-carbonyl-diimidazole, 1-ethyl-3-(3-dimethylaminopropyl)carbodiimide hydrochloride, 1-(dimethylcarbamoyl)-4-(2-sulfoethyl)pyridinium hydroxide inner salt and 4-(4,6-dimethoxy-1,3,5-triazine-2-yl)-4-methylmorpholinium chloride.

Among the above-described condensing agents, 4-(4,6-dimethoxy-1,3,5-triazine-2-yl)-4-methylmorpholinium chloride (hereinafter, this condensing agent is also referred to as DMT-MM) is favorably used. When DMT-MM is used, reaction residue is small, and a higher reaction yield can be achieved. Since the dehydration condensation reaction of the carboxyl group used in the formation of the amide bond is a reversible reaction, the formation of the amide bond under dehydration conditions is favorable. Therefore, when a carbodiimide type condensing agent heretofore used is used, the pigment needs to be dispersed in oil. The investigation by the present inventors has revealed that the formation of the amide bond in oil is low in yield, and difficulty is encountered on removal of unnecessary components such as residue after reaction. Since DMT-MM permits advancing the reaction in water and at room temperature, handling is extremely easy. In addition, since by-products formed upon the use of DMT-MM are water-soluble, the by-products can be easily removed.

As the amine compound usable in the production process of the self-dispersion pigment according to the present invention, any compound may be favorably used so far as it is a compound having a nonionic molecular chain and an amino group. Specific examples of the amine compound include diglycolamine, diethanolamine, polyoxyalkyleneamines [JEFFAMINE M-600 (another name: XTJ-505, product of HUNTSMAN), JEFFAMINE M-1000 (another name: XTJ-506, product of HUNTSMAN), JEFFAMINE M-2005 (another name: XTJ-507, product of HUNTSMAN), JEFFAMINE M-2070 (product of HUNTSMAN), JEFFAMINE XTJ-435 (product of HUNTSMAN), JEFFAMINE XTJ-436 (product of HUNTSMAN), methoxy-PEG-amine (SUNBRIGHT MEPA, product of Nichiyu Chemical Co., Ltd.), and hydroxy-PEG-amine (SUNBRIGHT HO, product of Nichiyu Chemical Co., Ltd.)], benzylamine, dibenzylamine, glycine-tert-butyl, methylamine, n-butyl-amine, isobutylamine, tert-butylamine, cyclopentylamine, methoxypolyethyleneglycolamine. Among these, polyoxy-alkyleneamine JEFFAMINE XTJ-436 (product of HUNTSMAN), benzylamine, dibenzylamine and cyclopentylamine are favorable because a hydrocarbon having a cyclic hydrocarbon is formed as the nonionic molecular chain upon the formation of the amide bond. In addition, diglycolamine, and polyoxyalkyleneamines [JEFFAMINE M-600 (another name: XTJ-505, product of HUNTSMAN), JEFFAMINE M-1000 (another name: XTJ-506, product of HUNTSMAN), JEFFAMINE M-2005 (another name: XTJ-507, product of HUNTSMAN), JEFFAMINE M-2070 (product of HUNTSMAN), JEFFAMINE XTJ-435 (product of HUNTSMAN), methoxyPEGamine (SUNBRIGHT MEPA, product of Nichiyu Chemical Co., Ltd.) and hydroxyPEGamine (SUNBRIGHT HO, product of Nichiyu Chemical Co., Ltd.)] are favorable because an alkyl ether is formed as the nonionic molecular chain upon the formation of the amide bond.

In the present invention, it is preferable to remove by-products of the reaction and reaction residue, which are components unnecessary to the self-dispersion pigment and the ink, after conducting the step of forming the amide bond. Specifically, the unnecessary components can be removed by means of an electrophoresis method, ultrafiltration method, centrifugation method or filtration method.

[Ink Jet Recording Method]

The ink jet recording method using the ink set according to the present invention is a method of applying the ink and the liquid composition to a recording medium so as to come into contact with each other. By using this recording method, the aggregating ability of the self-dispersion pigment in the ink can be improved, so that the fixability of the self-dispersion pigment can be improved, and bleeding caused upon contact between inks can be reduced.

In the present invention, an ink jet recording system is used upon the application of the ink to the recording medium. However, another system than the ink jet recording system may also be used upon the application of the liquid composition to the recording medium. Specifically, a coating method by a roller coating, bar coating or spray coating system is mentioned. The use of the coating method is preferable because the ink and the liquid composition can be brought into contact with each other even when an image formed by the ink is in any form.

No particular limitation is imposed on the order of the application of the ink and the liquid composition to the recording medium. However, the liquid composition is favorably applied previously. When the liquid composition is applied to the recording medium in advance, the influence of the penetrating speed of the ink can be reduced to efficiently cause an aggregation reaction.

EXAMPLES

The present invention will hereinafter be described more specifically by the following Examples and Comparative Examples. However, the present invention is not limited by these examples unless going beyond the gist of the present invention. Incidentally, all designations of "part" or "parts" and "%" in the following description mean part or parts by mass and % by mass unless expressly noted.

[Dispersion Liquid 1]

To 10 g of a pigment (Printex 80, product of Evonik Co.), were added 200 g of ion-exchanged water and 125 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 1 containing an oxidized pigment. The pigment concentration in Dispersion Liquid 1 was 10%.

[Self-Dispersion Pigment Dispersion Liquid 1]

After 30 g of Dispersion Liquid 1 was sampled, 1.52 g of diglycolamine and 0.47 g of DMT-MM were added to the Dispersion Liquid 1 sampled, and the resultant mixture was stirred for 24 hours at room temperature. Thereafter, filtration and purification were conducted by an ultrafiltration method. After the purification, Self-Dispersion Pigment Dispersion Liquid 1 containing Self-Dispersion Pigment 1 being a pigment to which an anionic group was directly bonded and a nonionic molecular chain was bonded through an amide bond was obtained. The pigment concentration in Self-Dispersion Pigment Dispersion Liquid 1 was 6%.

The total amount of the ionic group and nonionic molecular chain of Self-Dispersion Pigment 1 was determined. As a result, the total amount was 0.78 mmol/g. The amount of the ionic group was determined. As a result, it was 0.35 mmol/g. Accordingly, the amount of the nonionic molecular chain was found to be 0.43 mmol/g by calculation.

[Dispersion Liquid 2]

To 10 g of a pigment (Printex 80, product of Evonik Co.), were added 200 g of ion-exchanged water and 80 g of sodium hypochlorite, and the resultant mixture was stirred for 48 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 2 containing an oxidized pigment. The pigment concentration in Dispersion Liquid 2 was 10%.

[Self-Dispersion Pigment Dispersion Liquid 2]

After 30 g of Dispersion Liquid 2 was sampled, 1.87 g of diglycolamine and 0.57 g of DMT-MM were added to the Dispersion Liquid 2 sampled, and the resultant mixture was stirred for 24 hours at room temperature. Thereafter, filtration and purification were conducted by an ultrafiltration method. After the purification, Self-Dispersion Pigment Dispersion Liquid 2 containing Self-Dispersion Pigment 2 being a pigment to which an anionic group was directly bonded and a nonionic molecular chain was bonded through an amide bond was obtained. The pigment concentration in Self-Dispersion Pigment Dispersion Liquid 2 was 6%.

The total amount of the ionic group and nonionic molecular chain of Self-Dispersion Pigment 2 was determined. As a result, the total amount was 1.19 mmol/g. The amount of the ionic group was determined. As a result, it was 0.66 mmol/g. Accordingly, the amount of the nonionic molecular chain was found to be 0.53 mmol/g by calculation.

[Dispersion Liquid 3]

To 10 g of a pigment (Printex 80, product of Evonik Co.), were added 200 g of ion-exchanged water and 80 g of sodium hypochlorite, and the resultant mixture was stirred for 72 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 3 containing an oxidized pigment. The pigment concentration in Dispersion Liquid 3 was 10%.

[Self-Dispersion Pigment Dispersion Liquid 3]

After 30 g of Dispersion Liquid 3 was sampled, 1.45 g of diglycolamine and 0.44 g of DMT-MM were added to the Dispersion Liquid 3 sampled, and the resultant mixture was stirred for 24 hours at room temperature. Thereafter, filtration and purification were conducted by an ultrafiltration method. After the purification, Self-Dispersion Pigment Dispersion Liquid 3 containing Self-Dispersion Pigment 3 being a pigment to which an anionic group was directly bonded and a nonionic molecular chain was bonded through an amide bond was obtained. The pigment concentration in Self-Dispersion Pigment Dispersion Liquid 3 was 6%.

The total amount of the ionic group and nonionic molecular chain of Self-Dispersion Pigment 3 was determined. As a result, the total amount was 1.61 mmol/g. The amount of the ionic group was determined. As a result, it was 1.20 mmol/g. Accordingly, the amount of the nonionic molecular chain was found to be 0.41 mmol/g by calculation.

[Dispersion Liquid 4]

To 10 g of a pigment (Printex 80, product of Evonik Co.), were added 200 g of ion-exchanged water and 50 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 4 containing an oxidized pigment. The pigment concentration in Dispersion Liquid 4 was 10%.

[Self-Dispersion Pigment Dispersion Liquid 4]

After 30 g of Dispersion Liquid 4 was sampled, 0.64 g of diglycolamine and 0.19 g of DMT-MM were added to the Dispersion Liquid 4 sampled, and the resultant mixture was stirred for 24 hours at room temperature. Thereafter, filtration and purification were conducted by an ultrafiltration method. After the purification, Self-Dispersion Pigment Dispersion Liquid 4 containing Self-Dispersion Pigment 4 being a pigment to which an anionic group was directly bonded and a nonionic molecular chain was bonded through an amide bond was obtained. The pigment concentration in Self-Dispersion Pigment Dispersion Liquid 4 was 6%.

The total amount of the ionic group and nonionic molecular chain of Self-Dispersion Pigment 4 was determined. As a result, the total amount was 0.38 mmol/g. The amount of the ionic group was determined. As a result, it was 0.20 mmol/g.

Accordingly, the amount of the nonionic molecular chain was found to be 0.18 mmol/g by calculation.

[Dispersion Liquid 5]

To 10 g of a pigment (Printex 80, product of Evonik Co.), were added 200 g of ion-exchanged water and 12 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 5 containing an oxidized pigment. The pigment concentration in Dispersion Liquid 5 was 10%.

[Self-Dispersion Pigment Dispersion Liquid 5]

After 30 g of Dispersion Liquid 5 was sampled, 0.39 g of diglycolamine and 0.12 g of DMT-MM were added to the Dispersion Liquid 5 sampled, and the resultant mixture was stirred for 24 hours at room temperature. Thereafter, filtration and purification were conducted by an ultrafiltration method. After the purification, Self-Dispersion Pigment Dispersion Liquid 5 containing Self-Dispersion Pigment 5 being a pigment to which an anionic group was directly bonded and a nonionic molecular chain was bonded through an amide bond was obtained. The pigment concentration in Self-Dispersion Pigment Dispersion Liquid 5 was 6%.

The total amount of the ionic group and nonionic molecular chain of Self-Dispersion Pigment 5 was determined. As a result, the total amount was 0.20 mmol/g. The amount of the ionic group was determined. As a result, it was 0.09 mmol/g. Accordingly, the amount of the nonionic molecular chain was found to be 0.11 mmol/g by calculation.

[Dispersion Liquid 6]

To 10 g of a pigment (Printex 80, product of Evonik Co.), were added 200 g of ion-exchanged water and 10 g of sodium hypochlorite, and the resultant mixture was stirred for 12 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 6 containing an oxidized pigment. The pigment concentration in Dispersion Liquid 6 was 10%.

[Self-Dispersion Pigment Dispersion Liquid 6]

After 30 g of Dispersion Liquid 6 was sampled, 0.28 g of diglycolamine and 0.09 g of DMT-MM were added to the Dispersion Liquid 6 sampled, and the resultant mixture was stirred for 24 hours at room temperature. Thereafter, filtration and purification were conducted by an ultrafiltration method. After the purification, Self-Dispersion Pigment Dispersion Liquid 6 containing Self-Dispersion Pigment 6 being a pigment to which an anionic group was directly bonded and a nonionic molecular chain was bonded through an amide bond was obtained. The pigment concentration in Self-Dispersion Pigment Dispersion Liquid 6 was 6%.

The total amount of the ionic group and nonionic molecular chain of Self-Dispersion Pigment 6 was determined. As a result, the total amount was 0.15 mmol/g. The amount of the ionic group was determined. As a result, it was 0.07 mmol/g. Accordingly, the amount of the nonionic molecular chain was found to be 0.08 mmol/g by calculation.

[Self-Dispersion Pigment Dispersion Liquid 7]

An operation was conducted in the same manner as in the production process of Self-Dispersion Pigment Dispersion Liquid 1 except that after 30 g of Dispersion Liquid 1 was sampled, 2.16 g of diglycolamine and 0.66 g of DMT-MM were added to the Dispersion Liquid 1 sampled. After the above operation, Self-Dispersion Pigment Dispersion Liquid 7 containing Self-Dispersion Pigment 7 being a pigment to which an anionic group was directly bonded and a nonionic molecular chain was bonded through an amide bond was obtained. The pigment concentration in Self-Dispersion Pigment Dispersion Liquid 7 was 6%.

The total amount of the ionic group and nonionic molecular chain of Self-Dispersion Pigment 7 was determined. As a result, the total amount was 0.78 mmol/g. The amount of the ionic group was determined. As a result, it was 0.17 mmol/g. Accordingly, the amount of the nonionic molecular chain was found to be 0.61 mmol/g by calculation.

[Self-Dispersion Pigment Dispersion Liquid 8]

An operation was conducted in the same manner as in the production process of Self-Dispersion Pigment Dispersion Liquid 1 except that after 30 g of Dispersion Liquid 1 was sampled, 2.37 g of diglycolamine and 0.72 g of DMT-MM were added to the Dispersion Liquid 1 sampled. After the above operation, Self-Dispersion Pigment Dispersion Liquid 8 containing Self-Dispersion Pigment 8 being a pigment to which an anionic group was directly bonded and a nonionic molecular chain was bonded through an amide bond was obtained. The pigment concentration in Self-Dispersion Pigment Dispersion Liquid 8 was 6%.

The total amount of the ionic group and nonionic molecular chain of Self-Dispersion Pigment 8 was determined. As a result, the total amount was 0.78 mmol/g. The amount of the ionic group was determined. As a result, it was 0.11 mmol/g. Accordingly, the amount of the nonionic molecular chain was found to be 0.67 mmol/g by calculation.

[Self-Dispersion Pigment Dispersion Liquid 9]

An operation was conducted in the same manner as in the production process of Self-Dispersion Pigment Dispersion Liquid 1 except that after 30 g of Dispersion Liquid 1 was sampled, 2.51 g of diglycolamine and 0.77 g of DMT-MM were added to the Dispersion Liquid 1 sampled. After the above operation, Self-Dispersion Pigment Dispersion Liquid 9 containing Self-Dispersion Pigment 9 being a pigment to which an anionic group was directly bonded and a nonionic molecular chain was bonded through an amide bond was obtained. The pigment concentration in Self-Dispersion Pigment Dispersion Liquid 9 was 6%.

The total amount of the ionic group and nonionic molecular chain of Self-Dispersion Pigment 9 was determined. As a result, the total amount was 0.78 mmol/g. The amount of the ionic group was determined. As a result, it was 0.07 mmol/g. Accordingly, the amount of the nonionic molecular chain was found to be 0.71 mmol/g by calculation.

[Self-Dispersion Pigment Dispersion Liquid 10]

An operation was conducted in the same manner as in the production process of Self-Dispersion Pigment Dispersion Liquid 1 except that after 30 g of Dispersion Liquid 1 was sampled, 2.65 g of diglycolamine and 0.81 g of DMT-MM were added to the Dispersion Liquid 1 sampled. After the above operation, Self-Dispersion Pigment Dispersion Liquid 10 containing Self-Dispersion Pigment 10 being a pigment to which an anionic group was directly bonded and a nonionic molecular chain was bonded through an amide bond was obtained. The pigment concentration in Self-Dispersion Pigment Dispersion Liquid 10 was 6%.

The total amount of the ionic group and nonionic molecular chain of Self-Dispersion Pigment 10 was determined. As a result, the total amount was 0.78 mmol/g. The amount of the ionic group was determined. As a result, it was 0.03 mmol/g. Accordingly, the amount of the nonionic molecular chain was found to be 0.75 mmol/g by calculation.

[Self-Dispersion Pigment Dispersion Liquid 11]

An operation was conducted in the same manner as in the production process of Self-Dispersion Pigment Dispersion Liquid 1 except that after 30 g of Dispersion Liquid 1 was sampled, 0.53 g of diglycolamine and 0.16 g of DMT-MM were added to the Dispersion Liquid 1 sampled. After the above operation, Self-Dispersion Pigment Dispersion Liquid 11 containing Self-Dispersion Pigment 11 being a pigment to which an anionic group was directly bonded and a nonionic molecular chain was bonded through an amide bond was obtained. The pigment concentration in Self-Dispersion Pigment Dispersion Liquid 11 was 6%.

The total amount of the ionic group and nonionic molecular chain of Self-Dispersion Pigment 11 was determined. As a result, the total amount was 0.78 mmol/g. The amount of the ionic group was determined. As a result, it was 0.63 mmol/g. Accordingly, the amount of the nonionic molecular chain was found to be 0.15 mmol/g by calculation.

[Self-Dispersion Pigment Dispersion Liquid 12]

An operation was conducted in the same manner as in the production process of Self-Dispersion Pigment Dispersion Liquid 1 except that after 30 g of Dispersion Liquid 1 was sampled, 0.32 g of diglycolamine and 0.10 g of DMT-MM were added to the Dispersion Liquid 1 sampled. After the above operation, Self-Dispersion Pigment Dispersion Liquid 12 containing Self-Dispersion Pigment 12 being a pigment to which an anionic group was directly bonded and a nonionic molecular chain was bonded through an amide bond was obtained. The pigment concentration in Self-Dispersion Pigment Dispersion Liquid 12 was 6%.

The total amount of the ionic group and nonionic molecular chain of Self-Dispersion Pigment 12 was determined. As a result, the total amount was 0.78 mmol/g. The amount of the ionic group was determined. As a result, it was 0.69 mmol/g. Accordingly, the amount of the nonionic molecular chain was found to be 0.09 mmol/g by calculation.

[Self-Dispersion Pigment Dispersion Liquid 13]

An operation was conducted in the same manner as in the production process of Self-Dispersion Pigment Dispersion Liquid 1 except that after 30 g of Dispersion Liquid 1 was sampled, 141 mg of diglycolamine and 43 mg of DMT-MM were added to the Dispersion Liquid 1 sampled. After the above operation, Self-Dispersion Pigment Dispersion Liquid 13 containing Self-Dispersion Pigment 13 being a pigment to which an anionic group was directly bonded and a nonionic molecular chain was bonded through an amide bond was obtained. The pigment concentration in Self-Dispersion Pigment Dispersion Liquid 13 was 6%.

The total amount of the ionic group and nonionic molecular chain of Self-Dispersion Pigment 13 was determined. As a result, the total amount was 0.78 mmol/g. The amount of the ionic group was determined. As a result, it was 0.74 mmol/g. Accordingly, the amount of the nonionic molecular chain was found to be 0.04 mmol/g by calculation.

[Self-Dispersion Pigment Dispersion Liquid 14]

An operation was conducted in the same manner as in the production process of Self-Dispersion Pigment Dispersion Liquid 1 except that after 30 g of Dispersion Liquid 1 was sampled, 35 mg of diglycolamine and 11 mg of DMT-MM were added to the Dispersion Liquid 1 sampled. After the above operation, Self-Dispersion Pigment Dispersion Liquid 14 containing Self-Dispersion Pigment 14 being a pigment to which an anionic group was directly bonded and a nonionic molecular chain was bonded through an amide bond was obtained. The pigment concentration in Self-Dispersion Pigment Dispersion Liquid 14 was 6%.

The total amount of the ionic group and nonionic molecular chain of Self-Dispersion Pigment 14 was determined. As a result, the total amount was 0.78 mmol/g. The amount of the ionic group was determined. As a result, it was 0.77 mmol/g. Accordingly, the amount of the nonionic molecular chain was found to be 0.01 mmol/g by calculation.

[Self-Dispersion Pigment Dispersion Liquid 15]

An operation was conducted in the same manner as in the production process of Self-Dispersion Pigment Dispersion Liquid 1 except that after 30 g of Dispersion Liquid 1 was sampled, 1.41 g of diglycolamine and 0.43 g of DMT-MM were added to the Dispersion Liquid 1 sampled. After the above operation, Self-Dispersion Pigment Dispersion Liquid 15 containing Self-Dispersion Pigment 15 being a pigment to which an anionic group was directly bonded and a nonionic molecular chain was bonded through an amide bond was obtained. The pigment concentration in Self-Dispersion Pigment Dispersion Liquid 15 was 6%.

The total amount of the ionic group and nonionic molecular chain of Self-Dispersion Pigment 15 was determined. As a result, the total amount was 0.78 mmol/g. The amount of the ionic group was determined. As a result, it was 0.38 mmol/g. Accordingly, the amount of the nonionic molecular chain was found to be 0.40 mmol/g by calculation.

[Dispersion Liquid 16]

To 10 g of a pigment (Printex 80, product of Evonik Co.), were added 200 g of ion-exchanged water and 100 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 16 containing an oxidized pigment. The pigment concentration in Dispersion Liquid 16 was 10%.

[Self-Dispersion Pigment Dispersion Liquid 16]

After 30 g of Dispersion Liquid 16 was sampled, 1.05 g of benzylamine and 0.31 g of DMT-MM were added to the Dispersion Liquid 16 sampled, and the resultant mixture was stirred for 24 hours at room temperature. Thereafter, filtration and purification were conducted by an ultrafiltration method. After the purification, Self-Dispersion Pigment Dispersion Liquid 16 containing Self-Dispersion Pigment 16 being a pigment to which an anionic group was directly bonded and a nonionic molecular chain was bonded through an amide bond was obtained. The pigment concentration in Self-Dispersion Pigment Dispersion Liquid 16 was 6%.

The total amount of the ionic group and nonionic molecular chain of Self-Dispersion Pigment 16 was determined. As a result, the total amount was 0.63 mmol/g. The amount of the ionic group was determined. As a result, it was 0.34 mmol/g. Accordingly, the amount of the nonionic molecular chain was found to be 0.29 mmol/g by calculation.

[Dispersion Liquid 17]

To 10 g of a pigment (Printex 80, product of Evonik Co.), were added 200 g of ion-exchanged water and 100 g of sodium hypochlorite, and the resultant mixture was stirred for 48 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 17 containing an oxidized pigment. The pigment concentration in Dispersion Liquid 17 was 10%.

[Self-Dispersion Pigment Dispersion Liquid 17]

After 30 g of Dispersion Liquid 17 was sampled, 2.02 g of benzylamine and 0.61 g of DMT-MM were added to the Dispersion Liquid 17 sampled, and the resultant mixture was stirred for 24 hours at room temperature. Thereafter, filtration and purification were conducted by an ultrafiltration method. After the purification, Self-Dispersion Pigment Dispersion Liquid 17 containing Self-Dispersion Pigment 17 being a pigment to which an anionic group was directly bonded and a nonionic molecular chain was bonded through an amide bond was obtained. The pigment concentration in Self-Dispersion Pigment Dispersion Liquid 17 was 6%.

The total amount of the ionic group and nonionic molecular chain of Self-Dispersion Pigment 17 was determined. As a result, the total amount was 1.35 mmol/g. The amount of the ionic group was determined. As a result, it was 0.79 mmol/g. Accordingly, the amount of the nonionic molecular chain was found to be 0.56 mmol/g by calculation.

[Dispersion Liquid 18]

To 10 g of a pigment (Printex 80, product of Evonik Co.), were added 200 g of ion-exchanged water and 100 g of sodium hypochlorite, and the resultant mixture was stirred for 72 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 18 containing an oxidized pigment. The pigment concentration in Dispersion Liquid 18 was 10%.

[Self-Dispersion Pigment Dispersion Liquid 18]

After 30 g of Dispersion Liquid 18 was sampled, 2.38 g of benzylamine and 0.71 g of DMT-MM were added to the Dispersion Liquid 18 sampled, and the resultant mixture was stirred for 24 hours at room temperature. Thereafter, filtration and purification were conducted by an ultrafiltration method. After the purification, Self-Dispersion Pigment Dispersion Liquid 18 containing Self-Dispersion Pigment 18 being a pigment to which an anionic group was directly bonded and a nonionic molecular chain was bonded through an amide bond was obtained. The pigment concentration in Self-Dispersion Pigment Dispersion Liquid 18 was 6%.

The total amount of the ionic group and nonionic molecular chain of Self-Dispersion Pigment 18 was determined. As a result, the total amount was 1.71 mmol/g. The amount of the ionic group was determined. As a result, it was 1.05 mmol/g. Accordingly, the amount of the nonionic molecular chain was found to be 0.66 mmol/g by calculation.

[Dispersion Liquid 19]

To 10 g of a pigment (Printex 80, product of Evonik Co.), were added 200 g of ion-exchanged water and 50 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 19 containing an oxidized pigment. The pigment concentration in Dispersion Liquid 19 was 10%.

[Self-Dispersion Pigment Dispersion Liquid 19]

After 30 g of Dispersion Liquid 19 was sampled, 0.54 g of benzylamine and 0.16 g of DMT-MM were added to the Dispersion Liquid 19 sampled, and the resultant mixture was stirred for 4 hours at room temperature. Thereafter, filtration and purification were conducted by an ultrafiltration method. After the purification, Self-Dispersion Pigment Dispersion Liquid 19 containing Self-Dispersion Pigment 19 being a pigment to which an anionic group was directly bonded and a nonionic molecular chain was bonded through an amide bond was obtained. The pigment concentration in Self-Dispersion Pigment Dispersion Liquid 19 was 6%.

The total amount of the ionic group and nonionic molecular chain of Self-Dispersion Pigment 19 was determined. As a result, the total amount was 0.38 mmol/g. The amount of the ionic group was determined. As a result, it was 0.23 mmol/g. Accordingly, the amount of the nonionic molecular chain was found to be 0.15 mmol/g by calculation.

[Dispersion Liquid 20]

To 10 g of a pigment (Printex 80, product of Evonik Co.), were added 200 g of ion-exchanged water and 15 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 20 containing an oxidized pigment. The pigment concentration in Dispersion Liquid 20 was 10%.

[Self-Dispersion Pigment Dispersion Liquid 20]

After 30 g of Dispersion Liquid 20 was sampled, 0.43 g of benzylamine and 0.13 g of DMT-MM were added to the Dispersion Liquid 20 sampled, and the resultant mixture was stirred for 24 hours at room temperature. Thereafter, filtration and purification were conducted by an ultrafiltration method. After the purification, Self-Dispersion Pigment Dispersion Liquid 20 containing Self-Dispersion Pigment 20 being a pigment to which an anionic group was directly bonded and a nonionic molecular chain was bonded through an amide bond was obtained. The pigment concentration in Self-Dispersion Pigment Dispersion Liquid 20 was 6%.

The total amount of the ionic group and nonionic molecular chain of Self-Dispersion Pigment 20 was determined. As a result, the total amount was 0.24 mmol/g. The amount of the ionic group was determined. As a result, it was 0.12 mmol/g. Accordingly, the amount of the nonionic molecular chain was found to be 0.12 mmol/g by calculation.

[Dispersion Liquid 21]

To 10 g of a pigment (Printex 80, product of Evonik Co.), were added 200 g of ion-exchanged water and 10 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method to obtain Dispersion Liquid 21 containing an oxidized pigment. The pigment concentration in Dispersion Liquid 21 was 10%.

[Self-Dispersion Pigment Dispersion Liquid 21]

After 30 g of Dispersion Liquid 21 was sampled, 0.36 g of benzylamine and 0.11 g of DMT-MM were added to the Dispersion Liquid 21 sampled, and the resultant mixture was stirred for 24 hours at room temperature. Thereafter, filtration and purification were conducted by an ultrafiltration method. After the purification, Self-Dispersion Pigment Dispersion Liquid 21 containing Self-Dispersion Pigment 21 being a pigment to which an anionic group was directly bonded and a nonionic molecular chain was bonded through an amide bond was obtained. The pigment concentration in Self-Dispersion Pigment Dispersion Liquid 22 was 6%.

The total amount of the ionic group and nonionic molecular chain of Self-Dispersion Pigment 21 was determined. As a result, the total amount was 0.18 mmol/g. The amount of the ionic group was determined. As a result, it was 0.08 mmol/g. Accordingly, the amount of the nonionic molecular chain was found to be 0.10 mmol/g by calculation.

[Self-Dispersion Pigment Dispersion Liquid 22]

An operation was conducted in the same manner as in the production process of Self-Dispersion Pigment Dispersion Liquid 16 except that after 30 g of Dispersion Liquid 16 was sampled, 1.77 g of benzylamine and 0.53 g of DMT-MM were added to the Dispersion Liquid 16 sampled. After the above operation, Self-Dispersion Pigment Dispersion Liquid 22 containing Self-Dispersion Pigment 22 being a pigment to which an anionic group was directly bonded and a nonionic molecular chain was bonded through an amide bond was obtained. The pigment concentration in Self-Dispersion Pigment Dispersion Liquid 21 was 6%.

The total amount of the ionic group and nonionic molecular chain of Self-Dispersion Pigment 22 was determined. As a result, the total amount was 0.63 mmol/g. The amount of the ionic group was determined. As a result, it was 0.14 mmol/g. Accordingly, the amount of the nonionic molecular chain was found to be 0.49 mmol/g by calculation.

[Self-Dispersion Pigment Dispersion Liquid 23]

An operation was conducted in the same manner as in the production process of Self-Dispersion Pigment Dispersion Liquid 16 except that after 30 g of Dispersion Liquid 16 was sampled, 1.98 g of benzylamine and 0.59 g of DMT-MM were added to the Dispersion Liquid 16 sampled. After the above operation, Self-Dispersion Pigment Dispersion Liquid 23 containing Self-Dispersion Pigment 23 being a pigment to which an anionic group was directly bonded and a nonionic molecular chain was bonded through an amide bond was obtained. The pigment concentration in Self-Dispersion Pigment Dispersion Liquid 23 was 6%.

The total amount of the ionic group and nonionic molecular chain of Self-Dispersion Pigment 23 was determined. As a result, the total amount was 0.63 mmol/g. The amount of the ionic group was determined. As a result, it was 0.08 mmol/g. Accordingly, the amount of the nonionic molecular chain was found to be 0.55 mmol/g by calculation.

[Self-Dispersion Pigment Dispersion Liquid 24]

An operation was conducted in the same manner as in the production process of Self-Dispersion Pigment Dispersion Liquid 16 except that after 30 g of Dispersion Liquid 16 was sampled, 2.09 g of benzylamine and 0.63 g of DMT-MM were added to the Dispersion Liquid 16 sampled. After the above operation, Self-Dispersion Pigment Dispersion Liquid 24 containing Self-Dispersion Pigment 24 being a pigment to which an anionic group was directly bonded and a nonionic molecular chain was bonded through an amide bond was obtained. The pigment concentration in Self-Dispersion Pigment Dispersion Liquid 24 was 6%.

The total amount of the ionic group and nonionic molecular chain of Self-Dispersion Pigment 24 was determined. As a result, the total amount was 0.63 mmol/g. The amount of the ionic group was determined. As a result, it was 0.05 mmol/g. Accordingly, the amount of the nonionic molecular chain was found to be 0.58 mmol/g by calculation.

[Self-Dispersion Pigment Dispersion Liquid 25]

An operation was conducted in the same manner as in the production process of Self-Dispersion Pigment Dispersion Liquid 16 except that after 30 g of Dispersion Liquid 16 was sampled, 2.16 g of benzylamine and 0.65 g of DMT-MM were added to the Dispersion Liquid 16 sampled. After the above operation, Self-Dispersion Pigment Dispersion Liquid 25 containing Self-Dispersion Pigment 25 being a pigment to which an anionic group was directly bonded and a nonionic molecular chain was bonded through an amide bond was obtained. The pigment concentration in Self-Dispersion Pigment Dispersion Liquid 25 was 6%.

The total amount of the ionic group and nonionic molecular chain of Self-Dispersion Pigment 25 was determined. As a result, the total amount was 0.63 mmol/g. The amount of the ionic group was determined. As a result, it was 0.03 mmol/g. Accordingly, the amount of the nonionic molecular chain was found to be 0.60 mmol/g by calculation.

[Self-Dispersion Pigment Dispersion Liquid 26]

An operation was conducted in the same manner as in the production process of Self-Dispersion Pigment Dispersion Liquid 16 except that after 30 g of Dispersion Liquid 16 was sampled, 0.47 g of benzylamine and 0.14 g of DMT-MM were added to the Dispersion Liquid 16 sampled. After the above operation, Self-Dispersion Pigment Dispersion Liquid 26 containing Self-Dispersion Pigment 26 being a pigment to which an anionic group was directly bonded and a nonionic molecular chain was bonded through an amide bond was obtained. The pigment concentration in Self-Dispersion Pigment Dispersion Liquid 26 was 6%.

The total amount of the ionic group and nonionic molecular chain of Self-Dispersion Pigment 26 was determined. As a result, the total amount was 0.63 mmol/g. The amount of the ionic group was determined. As a result, it was 0.50 mmol/g. Accordingly, the amount of the nonionic molecular chain was found to be 0.13 mmol/g by calculation.

[Self-Dispersion Pigment Dispersion Liquid 27]

An operation was conducted in the same manner as in the production process of Self-Dispersion Pigment Dispersion Liquid 16 except that after 30 g of Dispersion Liquid 16 was sampled, 0.25 g of benzylamine and 0.08 g of DMT-MM were added to the Dispersion Liquid 16 sampled. After the above operation, Self-Dispersion Pigment Dispersion Liquid 27 containing Self-Dispersion Pigment 27 being a pigment to which an anionic group was directly bonded and a nonionic molecular chain was bonded through an amide bond was obtained. The pigment concentration in Self-Dispersion Pigment Dispersion Liquid 27 was 6%.

The total amount of the ionic group and nonionic molecular chain of Self-Dispersion Pigment 27 was determined. As a result, the total amount was 0.63 mmol/g. The amount of the ionic group was determined. As a result, it was 0.56 mmol/g. Accordingly, the amount of the nonionic molecular chain was found to be 0.07 mmol/g by calculation.

[Self-Dispersion Pigment Dispersion Liquid 28]

An operation was conducted in the same manner as in the production process of Self-Dispersion Pigment Dispersion Liquid 16 except that after 30 g of Dispersion Liquid 16 was sampled, 108 mg of benzylamine and 32 mg of DMT-MM were added to the Dispersion Liquid 16 sampled. After the above operation, Self-Dispersion Pigment Dispersion Liquid 28 containing Self-Dispersion Pigment 28 being a pigment to which an anionic group was directly bonded and a nonionic molecular chain was bonded through an amide bond was obtained. The pigment concentration in Self-Dispersion Pigment Dispersion Liquid 28 was 6%.

The total amount of the ionic group and nonionic molecular chain of Self-Dispersion Pigment 28 was determined. As a result, the total amount was 0.63 mmol/g. The amount of the ionic group was determined. As a result, it was 0.60 mmol/g. Accordingly, the amount of the nonionic molecular chain was found to be 0.03 mmol/g by calculation.

[Self-Dispersion Pigment Dispersion Liquid 29]

An operation was conducted in the same manner as in the production process of Self-Dispersion Pigment Dispersion Liquid 16 except that after 30 g of Dispersion Liquid 16 was sampled, 36 mg of benzylamine and 11 mg of DMT-MM were added to the Dispersion Liquid 16 sampled. After the above operation, Self-Dispersion Pigment Dispersion Liquid 29 containing Self-Dispersion Pigment 29 being a pigment to which an anionic group was directly bonded and a nonionic molecular chain was bonded through an amide bond was obtained. The pigment concentration in Self-Dispersion Pigment Dispersion Liquid 29 was 6%.

The total amount of the ionic group and nonionic molecular chain of Self-Dispersion Pigment 29 was determined. As a result, the total amount was 0.63 mmol/g. The amount of the ionic group was determined. As a result, it was 0.62 mmol/g. Accordingly, the amount of the nonionic molecular chain was found to be 0.01 mmol/g by calculation.

[Self-Dispersion Pigment Dispersion Liquid 30]

An operation was conducted in the same manner as in the production process of Self-Dispersion Pigment Dispersion Liquid 16 except that after 30 g of Dispersion Liquid 16 was sampled, 0.16 g of DMT-MM was added to the Dispersion Liquid 16 sampled, and 1.00 g of dibenzylamine was added in place of benzylamine. After the above operation, Self-Dispersion Pigment Dispersion Liquid 30 containing Self-Dispersion Pigment 30 being a pigment to which an anionic group was directly bonded and a nonionic molecular chain was bonded through an amide bond was obtained. The pigment concentration in Self-Dispersion Pigment Dispersion Liquid 30 was 6%.

The total amount of the ionic group and nonionic molecular chain of Self-Dispersion Pigment 30 was determined. As a result, the total amount was 0.63 mmol/g. The amount of the ionic group was determined. As a result, it was 0.48 mmol/g. Accordingly, the amount of the nonionic molecular chain was found to be 0.15 mmol/g by calculation.

[Self-Dispersion Pigment Dispersion Liquid 31]

An operation was conducted in the same manner as in the production process of Self-Dispersion Pigment Dispersion Liquid 16 except that after 30 g of Dispersion Liquid 16 was sampled, 0.31 g of DMT-MM was added to the Dispersion Liquid 16 sampled, and 1.64 g of glycine tert-butyl hydrochloride was added in place of benzylamine. After the above operation, Self-Dispersion Pigment Dispersion Liquid 31 containing Self-Dispersion Pigment 31 being a pigment to which an anionic group was directly bonded and a nonionic molecular chain was bonded through an amide bond was obtained. The pigment concentration in Self-Dispersion Pigment Dispersion Liquid 31 was 6%.

The total amount of the ionic group and nonionic molecular chain of Self-Dispersion Pigment 31 was determined. As a result, the total amount was 0.63 mmol/g. The amount of the ionic group was determined. As a result, it was 0.34 mmol/g. Accordingly, the amount of the nonionic molecular chain was found to be 0.29 mmol/g by calculation.

[Self-Dispersion Pigment Dispersion Liquid 32]

An operation was conducted in the same manner as in the production process of Self-Dispersion Pigment Dispersion Liquid 16 except that after 30 g of Dispersion Liquid 16 was sampled, 0.34 g of DMT-MM was added to the Dispersion Liquid 16 sampled, and 0.32 g of methylamine was added in place of benzylamine. After the above operation, Self-Dispersion Pigment Dispersion Liquid 32 containing Self-Dispersion Pigment 32 being a pigment to which an anionic group was directly bonded and a nonionic molecular chain was bonded through an amide bond was obtained. The pigment concentration in Self-Dispersion Pigment Dispersion Liquid 32 was 6%.

The total amount of the ionic group and nonionic molecular chain of Self-Dispersion Pigment 32 was determined. As a result, the total amount was 0.63 mmol/g. The amount of the ionic group was determined. As a result, it was 0.32 mmol/g. Accordingly, the amount of the nonionic molecular chain was found to be 0.31 mmol/g by calculation.

[Self-Dispersion Pigment Dispersion Liquid 33]

An operation was conducted in the same manner as in the production process of Self-Dispersion Pigment Dispersion Liquid 16 except that after 30 g of Dispersion Liquid 16 was sampled, 0.31 g of DMT-MM was added to the Dispersion Liquid 16 sampled, and 0.71 g of n-butylamine was added in place of benzylamine. After the above operation, Self-Dispersion Pigment Dispersion Liquid 33 containing Self-Dispersion Pigment 33 being a pigment to which an anionic group was directly bonded and a nonionic molecular chain was bonded through an amide bond was obtained. The pigment concentration in Self-Dispersion Pigment Dispersion Liquid 33 was 6%.

The total amount of the ionic group and nonionic molecular chain of Self-Dispersion Pigment 33 was determined. As a result, the total amount was 0.63 mmol/g. The amount of the ionic group was determined. As a result, it was 0.34 mmol/g. Accordingly, the amount of the nonionic molecular chain was found to be 0.29 mmol/g by calculation.

[Self-Dispersion Pigment Dispersion Liquid 34]

An operation was conducted in the same manner as in the production process of Self-Dispersion Pigment Dispersion Liquid 16 except that after 30 g of Dispersion Liquid 16 was sampled, 0.31 g of DMT-MM was added to the Dispersion Liquid 16 sampled, and 0.71 g of isobutylamine was added in place of benzylamine. After the above operation, Self-Dispersion Pigment Dispersion Liquid 34 containing Self-Dispersion Pigment 34 being a pigment to which an anionic group was directly bonded and a nonionic molecular chain was bonded through an amide bond was obtained. The pigment concentration in Self-Dispersion Pigment Dispersion Liquid 34 was 6%.

The total amount of the ionic group and nonionic molecular chain of Self-Dispersion Pigment 34 was determined. As a result, the total amount was 0.63 mmol/g. The amount of the ionic group was determined. As a result, it was 0.34 mmol/g. Accordingly, the amount of the nonionic molecular chain was found to be 0.29 mmol/g by calculation.

[Self-Dispersion Pigment Dispersion Liquid 35]

An operation was conducted in the same manner as in the production process of Self-Dispersion Pigment Dispersion Liquid 16 except that after 30 g of Dispersion Liquid 16 was sampled, 0.31 g of DMT-MM was added to the Dispersion Liquid 16 sampled, and 0.71 g of tert-butylamine was added in place of benzylamine. After the above operation, Self-Dispersion Pigment Dispersion Liquid 35 containing Self-Dispersion Pigment 35 being a pigment to which an anionic group was directly bonded and a nonionic molecular chain was bonded through an amide bond was obtained. The pigment concentration in Self-Dispersion Pigment Dispersion Liquid 35 was 6%.

The total amount of the ionic group and nonionic molecular chain of Self-Dispersion Pigment 35 was determined. As a result, the total amount was 0.63 mmol/g. The amount of the ionic group was determined. As a result, it was 0.34 mmol/g. Accordingly, the amount of the nonionic molecular chain was found to be 0.29 mmol/g by calculation.

[Self-Dispersion Pigment Dispersion Liquid 36]

An operation was conducted in the same manner as in the production process of Self-Dispersion Pigment Dispersion Liquid 16 except that after 30 g of Dispersion Liquid 16 was sampled, 0.31 g of DMT-MM was added to the Dispersion Liquid 16 sampled, and 0.83 g of cyclopentylamine was added in place of benzylamine. After the above operation, Self-Dispersion Pigment Dispersion Liquid 36 containing Self-Dispersion Pigment 36 being a pigment to which an anionic group was directly bonded and a nonionic molecular chain was bonded through an amide bond was obtained. The pigment concentration in Self-Dispersion Pigment Dispersion Liquid 36 was 6%.

The total amount of the ionic group and nonionic molecular chain of Self-Dispersion Pigment 36 was determined. As a result, the total amount was 0.63 mmol/g. The amount of the ionic group was determined. As a result, it was 0.34 mmol/g. Accordingly, the amount of the nonionic molecular chain was found to be 0.29 mmol/g by calculation.

[Self-Dispersion Pigment Dispersion Liquid 37]

An operation was conducted in the same manner as in the production process of Self-Dispersion Pigment Dispersion Liquid 1 except that after 30 g of Dispersion Liquid 1 was sampled, 0.29 g of DMT-MM was added to the Dispersion Liquid 1 sampled, and 5.46 g of polyoxyalkyleneamine [JEFFAMINE M-600 (another name: XTJ-505, product of HUNTSMAN Co.)] having a weight-average molecular weight (hereinafter also referred to as Mw) of 600 was added in place of diglycolamine. After the above operation, Self-Dispersion Pigment Dispersion Liquid 37 containing Self-Dispersion Pigment 37 being a pigment to which an anionic group was directly bonded and a nonionic molecular chain was bonded through an amide bond was obtained. The pigment concentration in Self-Dispersion Pigment Dispersion Liquid 37 was 6%.

The total amount of the ionic group and nonionic molecular chain of Self-Dispersion Pigment 37 was determined. As a result, the total amount was 0.78 mmol/g. The amount of the ionic group was determined. As a result, it was 0.36 mmol/g. Accordingly, the amount of the nonionic molecular chain was found to be 0.42 mmol/g by calculation.

[Self-Dispersion Pigment Dispersion Liquid 38]

An operation was conducted in the same manner as in the production process of Self-Dispersion Pigment Dispersion Liquid 1 except that after 30 g of Dispersion Liquid 1 was sampled, 11 mg of DMT-MM was added to the Dispersion Liquid 1 sampled, and 202 mg of polyoxyalkyleneamine [JEFFAMINE M-600 (another name: XTJ-505, product of HUNTSMAN Co.)] having a Mw of 600 was added in place of diglycolamine. After the above operation, Self-Dispersion Pigment Dispersion Liquid 38 containing Self-Dispersion Pigment 38 being a pigment to which an anionic group was directly bonded and a nonionic molecular chain was bonded through an amide bond was obtained. The pigment concentration in Self-Dispersion Pigment Dispersion Liquid 38 was 6%.

The total amount of the ionic group and nonionic molecular chain of Self-Dispersion Pigment 38 was determined. As a result, the total amount was 0.78 mmol/g. The amount of the ionic group was determined. As a result, it was 0.77 mmol/g. Accordingly, the amount of the nonionic molecular chain was found to be 0.01 mmol/g by calculation.

[Self-Dispersion Pigment Dispersion Liquid 39]

An operation was conducted in the same manner as in the production process of Self-Dispersion Pigment Dispersion Liquid 1 except that after 30 g of Dispersion Liquid 1 was sampled, 0.37 g of DMT-MM was added to the Dispersion Liquid 1 sampled, and 22.90 g of polyoxyalkyleneamine [JEFFAMINE M-2005 (another name: XTJ-507, product of HUNTSMAN Co.)] having a Mw of 2,000 was added in place of diglycolamine. After the above operation, Self-Dispersion Pigment Dispersion Liquid 39 containing Self-Dispersion Pigment 39 being a pigment to which an anionic group was directly bonded and a nonionic molecular chain was bonded through an amide bond was obtained. The pigment concentration in Self-Dispersion Pigment Dispersion Liquid 39 was 6%.

The total amount of the ionic group and nonionic molecular chain of Self-Dispersion Pigment 39 was determined. As a result, the total amount was 0.78 mmol/g. The amount of the ionic group was determined. As a result, it was 0.34 mmol/g. Accordingly, the amount of the nonionic molecular chain was found to be 0.44 mmol/g by calculation.

[Self-Dispersion Pigment Dispersion Liquid 40]

An operation was conducted in the same manner as in the production process of Self-Dispersion Pigment Dispersion Liquid 1 except that after 30 g of Dispersion Liquid 1 was sampled, 11 mg of DMT-MM was added to the Dispersion Liquid 1 sampled, and 673 mg of polyoxyalkyleneamine [JEFFAMINE M-2005 (another name: XTJ-507, product of HUNTSMAN Co.)] having a Mw of 2,000 was added in place of diglycolamine. After the above operation, Self-Dispersion Pigment Dispersion Liquid 40 containing Self-Dispersion Pigment 40 being a pigment to which an anionic group was directly bonded and a nonionic molecular chain was bonded through an amide bond was obtained. The pigment concentration in Self-Dispersion Pigment Dispersion Liquid 40 was 6%.

The total amount of the ionic group and nonionic molecular chain of Self-Dispersion Pigment 40 was determined. As a result, the total amount was 0.78 mmol/g. The amount of the ionic group was determined. As a result, it was 0.77 mmol/g. Accordingly, the amount of the nonionic molecular chain was found to be 0.01 mmol/g by calculation.

[Self-Dispersion Pigment Dispersion Liquid 41]

To 10 g of a pigment (Printex 80, product of Evonik Co.), were added 200 g of ion-exchanged water and 50 g of sodium hypochlorite, and the resultant mixture was stirred for 24 hours at 105° C. After the stirring was stopped, and the mixture was cooled, solids were taken out by centrifugal separation. After 1,000 g of ion-exchanged water was added to the solids taken out, and stirring was conducted for 1 hour, filtration and purification were conducted by an ultrafiltration method. After the filtration and purification, an excessive amount of aqueous solution of hydrochloric acid was added, and stirring was conducted for 1 hour. After 1 hour, centrifugal separation was conducted for 30 minutes at 5,000 rpm to collect precipitate. After the precipitate collected was dehydrated and dried, 3 g of the precipitate was sampled. To 3 g of the solids samples were added 27 g of methyl ethyl ketone and 0.12 g of N,N-diisopropylcarbodiimide. After stirring was conducted for 1 hour, 1.05 g of benzylamine was added, and stirring was conducted for 48 hours at 60° C. After 48 hours, the solvent was removed, 1,000 g of ion-exchanged water was added, and filtration and purification were conducted by an ultrafiltration method to obtain Self-Dispersion Pigment Dispersion Liquid 41 containing Self-Dispersion Pigment 41 being a pigment to which an anionic group was directly bonded and a nonionic molecular chain was bonded through an amide bond. The pigment concentration in Self-Dispersion Pigment Dispersion Liquid 41 was 6%.

The total amount of the ionic group and nonionic molecular chain of Self-Dispersion Pigment 41 was determined. As a result, the total amount was 0.63 mmol/g. The amount of the ionic group was determined. As a result, it was 0.34 mmol/g. Accordingly, the amount of the nonionic molecular chain was found to be 0.29 mmol/g by calculation.

[Self-Dispersion Pigment Dispersion Liquid 42]

Dispersion Liquid 1 was used as it is, thereby obtaining Self-Dispersion Pigment Dispersion Liquid 42 containing Self-Dispersion Pigment 42 with COOH directly bonded to the pigment. The amount of the ionic group of Self-Dispersion Pigment 42 was 0.63 mmol/g, and the amount of the nonionic molecular chain was 0 mmol/g.

[Self-Dispersion Pigment Dispersion Liquid 43]

Dispersion Liquid 2 was used as it is, thereby obtaining Self-Dispersion Pigment Dispersion Liquid 43 containing Self-Dispersion Pigment 43 with COOH directly bonded to the pigment. The amount of the ionic group of Self-Dispersion Pigment 43 was 1.19 mmol/g, and the amount of the nonionic molecular chain was 0 mmol/g.

[Self-Dispersion Pigment Dispersion Liquid 44]

An operation was conducted in the same manner as in the production process of Self-Dispersion Pigment Dispersion Liquid 1 except that after 30 g of Dispersion Liquid 1 was sampled, 2.76 g of diethanolamine and 0.84 g of DMT-MM were added to the Dispersion Liquid 1 sampled. After the above operation, Self-Dispersion Pigment Dispersion Liquid 44 containing Self-Dispersion Pigment 44 being a pigment to which a nonionic molecular chain was bonded through an amide bond was obtained. The pigment concentration in Self-Dispersion Pigment Dispersion Liquid 44 was 6%.

The total amount of the ionic group and nonionic molecular chain of Self-Dispersion Pigment 44 was determined. As a result, the total amount was 0.78 mmol/g. The amount of the ionic group was determined. As a result, it was less than the limit of detection. Accordingly, the amount of the ionic group was regarded as 0 mmol/g. Accordingly, the amount of the nonionic molecular chain was found to be 0.78 mmol/g by calculation.

[Self-Dispersion Pigment Dispersion Liquid 45]

An operation was conducted in the same manner as in the production process of Self-Dispersion Pigment Dispersion Liquid 1 except that after 30 g of Dispersion Liquid 1 was sampled, 2.45 g of benzylamine and 0.74 g of DMT-MM were added to the Dispersion Liquid 1 sampled. After the above operation, Self-Dispersion Pigment Dispersion Liquid 45 containing Self-Dispersion Pigment 45 that was a pigment, to which a nonionic molecular chain was bonded through an amide bond, was obtained. The pigment concentration in Self-Dispersion Pigment Dispersion Liquid 45 was 6%.

The total amount of the ionic group and nonionic molecular chain of Self-Dispersion Pigment 45 was determined. As a result, the total amount was 0.63 mmol/g. The amount of the ionic group was determined. As a result, it was less than the limit of detection. Accordingly, the amount of the ionic group was regarded as 0 mmol/g. Accordingly, the amount of the nonionic molecular chain was found to be 0.63 mmol/g by calculation.

<Total Amount of Ionic Group and Nonionic Molecular Chain of Self-Dispersion Pigment>

After an aqueous solution of hydrochloric acid was added to a self-dispersion pigment dispersion liquid to adjust its pH to 1 or less, the dispersion liquid was stirred for 96 hours at 105° C. After the stirring, centrifugal separation was conducted for 30 minutes at 5,000 rpm by a centrifugal separator to collect a self-dispersion pigment precipitated. After the self-dispersion pigment was dehydrated, dried and then weighed, a known amount of sodium hydrogencarbonate was added, and the resultant mixture was stirred. After the stirring, centrifugal separation was conducted for 1 hour at 80,000 rpm by a centrifugal separator to collect a supernatant liquid. The supernatant liquid collected was weighed to conduct neutralization titration with 0.1N hydrochloric acid, thereby calculating the total amount of the ionic group and nonionic molecular chain of the self-dispersion pigment from the titer.

<Amount of Ionic Group of Self-Dispersion Pigment>

An excess amount of an aqueous solution of hydrochloric acid was added to a self-dispersion pigment dispersion liquid, and the resultant mixture was stirred for 24 hours at room temperature. After the stirring, centrifugal separation was conducted for 30 minutes at 5,000 rpm by a centrifugal separator to collect a self-dispersion pigment precipitated. After the self-dispersion pigment collected was dehydrated, dried and then weighed, a known amount of sodium hydrogencarbonate was added, and the resultant mixture was stirred. After the stirring, centrifugal separation was conducted for 1 hour at 80,000 rpm by a centrifugal separator to collect a supernatant liquid. The supernatant liquid collected was weighed to conduct neutralization titration with 0.1N hydrochloric acid, thereby calculating the amount of the ionic group of the self-dispersion pigment from the titer.

<Amount of Nonionic Molecular Chain of Self-Dispersion Pigment>

The amount of the nonionic molecular chain of the self-dispersion pigment was calculated by subtracting the amount of the ionic group in the self-dispersion pigment, which had been found by the above-described method, from the total amount of the ionic group and nonionic molecular chain in the self-dispersion pigment, which had been found by the above-described method.

The compositions and physical properties of Self-Dispersion Pigments 1 to 45 are shown collectively in Table 1. Incidentally, the unit of the amount of the ionic group, the unit of the amount of the nonionic molecular chain, and the unit of the total amount of the anionic group and nonionic molecular chain are all mmol/g.

TABLE 1

|  | Amount of ionic group | Amount of nonionic molecular chain | Total amount of ionic group and nonionic molecular chain | Proportion of ionic group to total amount | Amine compound |
|---|---|---|---|---|---|
| Self-Dispersion Pigment Dispersion Liquid 1 | 0.35 | 0.43 | 0.78 | 44.9 | Diglycol-amine |
| Self-Dispersion Pigment Dispersion Liquid 2 | 0.66 | 0.53 | 1.19 | 55.5 | Diglycol-amine |
| Self-Dispersion Pigment Dispersion Liquid 3 | 1.20 | 0.41 | 1.61 | 74.5 | Diglycol-amine |
| Self-Dispersion Pigment Dispersion Liquid 4 | 0.20 | 0.18 | 0.38 | 52.6 | Diglycol-amine |
| Self-Dispersion Pigment Dispersion Liquid 5 | 0.09 | 0.11 | 0.20 | 45.0 | Diglycol-amine |
| Self-Dispersion Pigment Dispersion Liquid 6 | 0.07 | 0.08 | 0.15 | 46.7 | Diglycol-amine |

TABLE 1-continued

| | Amount of ionic group | Amount of nonionic molecular chain | Total amount of ionic group and nonionic molecular chain | Proportion of ionic group to total amount | Amine compound |
|---|---|---|---|---|---|
| Self-Dispersion Pigment Dispersion Liquid 7 | 0.17 | 0.61 | 0.78 | 21.8 | Diglycol-amine |
| Self-Dispersion Pigment Dispersion Liquid 8 | 0.11 | 0.67 | 0.78 | 14.1 | Diglycol-amine |
| Self-Dispersion Pigment Dispersion Liquid 9 | 0.07 | 0.71 | 0.78 | 9.0 | Diglycol-amine |
| Self-Dispersion Pigment Dispersion Liquid 10 | 0.03 | 0.75 | 0.78 | 3.8 | Diglycol-amine |
| Self-Dispersion Pigment Dispersion Liquid 11 | 0.63 | 0.15 | 0.78 | 80.8 | Diglycol-amine |
| Self-Dispersion Pigment Dispersion Liquid 12 | 0.69 | 0.09 | 0.78 | 88.5 | Diglycol-amine |
| Self-Dispersion Pigment Dispersion Liquid 13 | 0.74 | 0.04 | 0.78 | 94.9 | Diglycol-amine |
| Self-Dispersion Pigment Dispersion Liquid 14 | 0.77 | 0.01 | 0.78 | 98.7 | Diglycol-amine |
| Self-Dispersion Pigment Dispersion Liquid 15 | 0.38 | 0.40 | 0.78 | 48.7 | Diglycol-amine |
| Self-Dispersion Pigment Dispersion Liquid 16 | 0.34 | 0.29 | 0.63 | 54.0 | Benzylamine |
| Self-Dispersion Pigment Dispersion Liquid 17 | 0.79 | 0.56 | 1.35 | 58.5 | Benzylamine |
| Self-Dispersion Pigment Dispersion Liquid 18 | 1.05 | 0.66 | 1.71 | 61.4 | Benzylamine |
| Self-Dispersion Pigment Dispersion Liquid 19 | 0.23 | 0.15 | 0.38 | 60.5 | Benzylamine |
| Self-Dispersion Pigment Dispersion Liquid 20 | 0.12 | 0.12 | 0.24 | 50.0 | Benzylamine |
| Self-Dispersion Pigment Dispersion Liquid 21 | 0.08 | 0.10 | 0.18 | 44.4 | Benzylamine |
| Self-Dispersion Pigment Dispersion Liquid 22 | 0.14 | 0.49 | 0.63 | 22.2 | Benzylamine |
| Self-Dispersion Pigment Dispersion Liquid 23 | 0.08 | 0.55 | 0.63 | 12.7 | Benzylamine |
| Self-Dispersion Pigment Dispersion Liquid 24 | 0.05 | 0.58 | 0.63 | 7.9 | Benzylamine |
| Self-Dispersion Pigment Dispersion Liquid 25 | 0.03 | 0.60 | 0.63 | 4.8 | Benzylamine |
| Self-Dispersion Pigment Dispersion Liquid 26 | 0.50 | 0.13 | 0.63 | 79.4 | Benzylamine |
| Self-Dispersion Pigment Dispersion Liquid 27 | 0.56 | 0.07 | 0.63 | 88.9 | Benzylamine |
| Self-Dispersion Pigment Dispersion Liquid 28 | 0.60 | 0.03 | 0.63 | 95.2 | Benzylamine |
| Self-Dispersion Pigment Dispersion Liquid 29 | 0.62 | 0.01 | 0.63 | 98.4 | Benzylamine |
| Self-Dispersion Pigment Dispersion Liquid 30 | 0.48 | 0.15 | 0.63 | 76.2 | Dibenzylamine |
| Self-Dispersion Pigment Dispersion Liquid 31 | 0.34 | 0.29 | 0.63 | 54.0 | Glycine tert-butyl |
| Self-Dispersion Pigment Dispersion Liquid 32 | 0.32 | 0.31 | 0.63 | 50.8 | Methylamine |
| Self-Dispersion Pigment Dispersion Liquid 33 | 0.34 | 0.29 | 0.63 | 54.0 | n-Butyl-amine |
| Self-Dispersion Pigment Dispersion Liquid 34 | 0.34 | 0.29 | 0.63 | 54.0 | iso-Butyl-amine |
| Self-Dispersion Pigment Dispersion Liquid 35 | 0.34 | 0.29 | 0.63 | 54.0 | tert-Butyl-amine |
| Self-Dispersion Pigment Dispersion Liquid 36 | 0.34 | 0.29 | 0.63 | 54.0 | Cyclopentyl-amine |
| Self-Dispersion Pigment Dispersion Liquid 37 | 0.36 | 0.42 | 0.78 | 46.2 | Polyoxy-alkyleneamine (Mw: 600) |
| Self-Dispersion Pigment Dispersion Liquid 38 | 0.77 | 0.01 | 0.78 | 98.7 | Polyoxy-alkyleneamine (Mw: 600) |
| Self-Dispersion Pigment Dispersion Liquid 39 | 0.34 | 0.44 | 0.78 | 43.6 | Polyoxy-alkyleneamine (Mw: 2000) |
| Self-Dispersion Pigment Dispersion Liquid 40 | 0.77 | 0.01 | 0.78 | 98.7 | Polyoxy-alkyleneamine (Mw: 2000) |
| Self-Dispersion Pigment Dispersion Liquid 41 | 0.34 | 0.29 | 0.63 | 54.0 | Benzylamine |

TABLE 1-continued

| | Amount of ionic group | Amount of nonionic molecular chain | Total amount of ionic group and nonionic molecular chain | Proportion of ionic group to total amount | Amine compound |
|---|---|---|---|---|---|
| Self-Dispersion Pigment Dispersion Liquid 42 | 0.63 | — | 0.63 | 100.0 | — |
| Self-Dispersion Pigment Dispersion Liquid 43 | 1.19 | — | 1.19 | 100.0 | — |
| Self-Dispersion Pigment Dispersion Liquid 44 | 0.00 | 0.78 | 0.78 | 0.0 | Diethanol-amine |
| Self-Dispersion Pigment Dispersion Liquid 45 | 0.00 | 0.63 | 0.63 | 0.0 | Benzylamine |

[Preparation of Ink]

Self-Dispersion Pigments 1 to 45 were then used to prepare ink jet aqueous inks. The composition of each ink jet aqueous ink is as shown below. The ink prepared by using Self-Dispersion Pigment 1 as the self-dispersion pigment is referred to as Ink Jet Aqueous Ink 1, and inks in which the number of the self-dispersion pigment corresponded to the number of the ink jet aqueous ink were successively prepared.

| Composition of ink jet aqueous ink | |
|---|---|
| Self-dispersion pigment | 3% by mass |
| Glycerol | 5% by mass |
| Polyethylene glycol (weight-average molecular weight: 1,000) | 5% by mass |
| Acetylenol 100 | 1% by mass |
| Ion-exchanged water | 86% by mass. |

<Evaluation of Ink Jet Aqueous Ink>

With respect to each of Ink Jet Aqueous Inks 1 to 45 obtained by the above-described operation, measurements of various physical properties and evaluation were conducted according to the following respective methods. In the evaluation of the respective ink jet aqueous inks, Ink Jet Aqueous Inks 1 to 41 were regarded as Examples 1 to 41, and Ink Jet Aqueous Inks 42 to 45 were regarded as Comparative Examples 1 to 4.

{Dispersion Stability}

With respect to each of Ink Jet Aqueous Inks 1 to 45 obtained by the above-described operation, the average particle size of the self-dispersion pigment was measured. Each ink jet aqueous ink was then placed in a glass sample bottle and stored for one month at 60° C. The particle size after stored for 2 weeks was measured. After the measurement, the particle size after stored for 1 month at 60° C. was measured again. The rates of change in average particle size after 2 weeks and after 1 month to the average particle size before storage were determined based on the measured data thus obtained. Incidentally, ELS-8000 (manufactured by Otsuka Electronics Co., Ltd.) was used for the measurement of the average particle size of the pigment. The rates of change in average particle size of the respective ink jet aqueous inks are shown in Tables 2 and 3. Incidentally, "–" in Tables 2 and 3 means that change in average particle size was too marked to conduct the measurement. In the present invention, when the rate of change in average particle size after stored for 1 month was 50% or less, that ink was regarded as having sufficient dispersion stability.

<Evaluation of Image Density of Ink and Bleeding>

A thermal ink jet recording apparatus, PIXUS Pro-9500 (manufactured by Canon Inc.), in which each ink jet aqueous ink had been provided, was used to form an image on Office Planner (A4-sized plain paper, product of Canon Inc.) as a recording medium. The image density and bleeding were evaluated from the image thus obtained.

[Image Density]

Each ink was applied on plain paper by means of the above-described recording apparatus to form a solid-printed image, and the image was then left to stand for 1 hour. After left to stand, the image density of the image was measured by Macbeth RD915. The results obtained by using the respective ink jet aqueous inks are shown in Table 2. In the evaluation of the inks in the present invention, an ink the image density of which was 0.90 or more was regarded as an ink having sufficient performance.

[Bleeding]

Each of the ink jet aqueous inks was used as a black ink, and PGI-2Y (yellow ink, product of Canon, Inc.) was used as a color ink.

The ink jet aqueous ink and the color ink were applied onto a recording medium with the above-described recording apparatus such that a solid print portion printed with the ink jet aqueous ink and a solid print portion printed with the color ink so as to adjoin the solid print portion printed with the ink jet aqueous ink were formed in the same scan. The thus-obtained print was binarized between the ink jet aqueous ink and the color ink using a camera to measure the maximum length of bleeding from a reference line (maximum bleeding length). The results obtained by using the respective ink jet aqueous inks are shown in Table 2. In the evaluation of the inks in the present invention, an ink the maximum length bleeding length of which was 35 μm or less was regarded as an ink having sufficient performance.

TABLE 2

| | | Self-dispersion pigment in ink | Rate of change in average particle size | | Image density | Maximum bleeding length |
|---|---|---|---|---|---|---|
| | | | 2 week | 1 month | | |
| Ex. 1 | Ink Jet Aqueous Ink 1 | Self-Dispersion Pigment 1 | 0% | 0% | 1.10 | 19 μM |

TABLE 2-continued

|  |  | Self-dispersion pigment in ink | Rate of change in average particle size 2 week | Rate of change in average particle size 1 month | Image density | Maximum bleeding length |
|---|---|---|---|---|---|---|
| Ex. 2 | Ink Jet Aqueous Ink 2 | Self-Dispersion Pigment 2 | 0% | 0% | 1.08 | 20 μM |
| Ex. 3 | Ink Jet Aqueous Ink 3 | Self-Dispersion Pigment 3 | 0% | 0% | 1.06 | 20 μM |
| Ex. 4 | Ink Jet Aqueous Ink 4 | Self-Dispersion Pigment 4 | 0% | 0% | 1.13 | 17 μM |
| Ex. 5 | Ink Jet Aqueous Ink 5 | Self-Dispersion Pigment 5 | 0% | 0% | 1.15 | 16 μM |
| Ex. 6 | Ink Jet Aqueous Ink 6 | Self-Dispersion Pigment 6 | 0% | 24% | 1.15 | 12 μM |
| Ex. 7 | Ink Jet Aqueous Ink 7 | Self-Dispersion Pigment 7 | 0% | 0% | 1.11 | 18 μM |
| Ex. 8 | Ink Jet Aqueous Ink 8 | Self-Dispersion Pigment 8 | 0% | 0% | 1.09 | 20 μM |
| Ex. 9 | Ink Jet Aqueous Ink 9 | Self-Dispersion Pigment 9 | 0% | 0% | 1.09 | 21 μM |
| Ex. 10 | Ink Jet Aqueous Ink 10 | Self-Dispersion Pigment 10 | 0% | 0% | 0.88 | 30 μM |
| Ex. 11 | Ink Jet Aqueous Ink 11 | Self-Dispersion Pigment 11 | 0% | 0% | 1.07 | 19 μM |
| Ex. 12 | Ink Jet Aqueous Ink 12 | Self-Dispersion Pigment 12 | 0% | 1% | 1.08 | 20 μM |
| Ex. 13 | Ink Jet Aqueous Ink 13 | Self-Dispersion Pigment 13 | 0% | 4% | 1.07 | 22 μM |
| Ex. 14 | Ink Jet Aqueous Ink 14 | Self-Dispersion Pigment 14 | 2% | 31% | 1.04 | 24 μM |
| Ex. 15 | Ink Jet Aqueous Ink 15 | Self-Dispersion Pigment 15 | 0% | 2% | 1.11 | 20 μM |
| Ex. 16 | Ink Jet Aqueous Ink 16 | Self-Dispersion Pigment 16 | 0% | 0% | 1.11 | 19 μM |
| Ex. 17 | Ink Jet Aqueous Ink 17 | Self-Dispersion Pigment 17 | 0% | 0% | 1.06 | 21 μM |
| Ex. 18 | Ink Jet Aqueous Ink 18 | Self-Dispersion Pigment 18 | 0% | 0% | 1.04 | 23 μM |
| Ex. 19 | Ink Jet Aqueous Ink 19 | Self-Dispersion Pigment 19 | 0% | 0% | 1.12 | 17 μM |
| Ex. 20 | Ink Jet Aqueous Ink 20 | Self-Dispersion Pigment 20 | 0% | 3% | 1.13 | 16 μM |
| Ex. 21 | Ink Jet Aqueous Ink 21 | Self-Dispersion Pigment 21 | 3% | 48% | 1.15 | 16 μM |
| Ex. 22 | Ink Jet Aqueous Ink 22 | Self-Dispersion Pigment 22 | 0% | 0% | 1.11 | 19 μM |
| Ex. 23 | Ink Jet Aqueous Ink 23 | Self-Dispersion Pigment 23 | 0% | 0% | 1.11 | 19 μM |
| Ex. 24 | Ink Jet Aqueous Ink 24 | Self-Dispersion Pigment 24 | 0% | 0% | 1.08 | 22 μM |
| Ex. 25 | Ink Jet Aqueous Ink 25 | Self-Dispersion Pigment 25 | 0% | 0% | 0.92 | 32 μM |
| Ex. 26 | Ink Jet Aqueous Ink 26 | Self-Dispersion Pigment 26 | 1% | 4% | 1.08 | 19 μM |
| Ex. 27 | Ink Jet Aqueous Ink 27 | Self-Dispersion Pigment 27 | 0% | 8% | 1.07 | 22 μM |
| Ex. 28 | Ink Jet Aqueous Ink 28 | Self-Dispersion Pigment 28 | 1% | 29% | 1.07 | 22 μM |
| Ex. 29 | Ink Jet Aqueous Ink 29 | Self-Dispersion Pigment 29 | 6% | 43% | 1.05 | 23 μm |
| Ex. 30 | Ink Jet Aqueous Ink 30 | Self-Dispersion Pigment 30 | 0% | 0% | 1.10 | 19 μm |
| Ex. 31 | Ink Jet Aqueous Ink 31 | Self-Dispersion Pigment 31 | 0% | 3% | 1.11 | 19 μm |
| Ex. 32 | Ink Jet Aqueous Ink 32 | Self-Dispersion Pigment 32 | 0% | 12% | 1.11 | 21 μm |
| Ex. 33 | Ink Jet Aqueous Ink 33 | Self-Dispersion Pigment 33 | 0% | 10% | 1.12 | 20 μm |
| Ex. 34 | Ink Jet Aqueous Ink 34 | Self-Dispersion Pigment 34 | 0% | 8% | 1.11 | 20 μm |
| Ex. 35 | Ink Jet Aqueous Ink 35 | Self-Dispersion Pigment 35 | 0% | 0% | 1.12 | 19 μm |
| Ex. 36 | Ink Jet Aqueous Ink 36 | Self-Dispersion Pigment 36 | 1% | 5% | 1.10 | 19 μm |
| Ex. 37 | Ink Jet Aqueous Ink 37 | Self-Dispersion Pigment 37 | 0% | 0% | 1.10 | 20 μm |
| Ex. 38 | Ink Jet Aqueous Ink 38 | Self-Dispersion Pigment 38 | 0% | 22% | 1.11 | 20 μm |

TABLE 2-continued

|  |  | Self-dispersion pigment in ink | Rate of change in average particle size | | Image density | Maximum bleeding length |
| --- | --- | --- | --- | --- | --- | --- |
|  |  |  | 2 week | 1 month |  |  |
| Ex. 39 | Ink Jet Aqueous Ink 39 | Self-Dispersion Pigment 39 | 0% | 0% | 1.10 | 20 μm |
| Ex. 40 | Ink Jet Aqueous Ink 40 | Self-Dispersion Pigment 40 | 0% | 12% | 1.09 | 22 μm |
| Ex. 41 | Ink Jet Aqueous Ink 41 | Self-Dispersion Pigment 41 | 0% | 0% | 1.11 | 19 μm |
| Comp. Ex. 1 | Ink Jet Aqueous Ink 42 | Self-Dispersion Pigment 42 | 20% | 362% | 1.11 | 18 μm |
| Comp. Ex. 2 | Ink Jet Aqueous Ink 43 | Self-Dispersion Pigment 43 | 11% | 208% | 1.00 | 29 μm |
| Comp. Ex. 3 | Ink Jet Aqueous Ink 44 | Self-Dispersion Pigment 44 | 0% | 0% | 0.82 | 42 μm |
| Comp. Ex. 3 | Ink Jet Aqueous Ink 45 | Self-Dispersion Pigment 45 | 0% | 0% | 0.85 | 38 μm |

<Evaluation of Ink Set>

[Preparation of Ink Set]

Each of Ink Jet Aqueous Inks 1 to 45 obtained by the above-described operation and Liquid Composition 1 having a composition shown below were used to prepare an ink set. The ink sets prepared were evaluated in the following manner. In the evaluation of the respective ink sets, Ink Jet Aqueous Inks 1 to 41 were regarded as Examples 42 to 82, and Ink Jet Aqueous Inks 42 to 45 were regarded as Comparative Examples 5 to 8.

| Composition of Liquid Composition 1 | |
| --- | --- |
| Magnesium nitrate hexahydrate | 10% by mass |
| 1,2,6-Hexanetriol | 30% by mass |
| Trimethylolpropane | 5% by mass |
| Acetylenol 100 | 1% by mass |
| Ion-exchanged water | 54% by mass. |

<Evaluation of Image Density of Ink and Bleeding>

A thermal ink jet recording apparatus, PIXUS Pro-9500 (manufactured by Canon Inc.) in which each ink jet aqueous ink had been provided was used to form an image. The image density and bleeding were evaluated from the image thus obtained. Incidentally, Office Planner (A4-sized plain paper, product of Canon Inc.) to which 2.4 g/m² of the liquid composition had been applied by a bar coater in advance was used as a recording medium.

[Image Density]

Each ink was applied on the recording medium to which the liquid composition had been applied by means of the above-described recording apparatus to form a solid-printed image, and the image was then left to stand for 1 hour. After left to stand, the image density of the image was measured by Macbeth RD915. The results obtained by using the respective ink jet aqueous inks are shown in Table 3. In the evaluation of the ink sets in the present invention, an ink set the image density of which was 1.10 or more was regarded as an ink set having sufficient performance.

[Bleeding]

Each of the ink jet aqueous inks was used as a black ink, and PGI-2Y (yellow ink, product of Canon, Inc.) was used as a color ink.

The ink jet aqueous ink and the color ink were applied onto a recording medium with the above-described recording apparatus such that a solid print portion printed with the ink jet aqueous ink and a solid print portion printed with the color ink so as to adjoin the solid print portion printed with the ink jet aqueous ink were formed in the same scan. The thus-obtained print was binarized between the ink jet aqueous ink and the color ink using a camera to measure the maximum length of bleeding from a reference line (maximum bleeding length). The results obtained by using the respective ink jet aqueous inks are shown in Table 3. In the evaluation of the ink sets in the present invention, an ink set the maximum length bleeding length of which was 20 μm or less was regarded as an ink set having sufficient performance.

TABLE 3

|  |  | Self-dispersion pigment in ink | Liquid composition | Rate of change in average particle size | | Image density | Maximum bleeding length |
| --- | --- | --- | --- | --- | --- | --- | --- |
|  |  |  |  | 2 week | 1 month |  |  |
| Ex. 42 | Ink Jet Aqueous Ink 1 | Self-Dispersion Pigment 1 | Liquid Composition 1 | 0% | 0% | 1.33 | 3 μm |
| Ex. 43 | Ink Jet Aqueous Ink 2 | Self-Dispersion Pigment 2 | Liquid Composition 1 | 0% | 0% | 1.4 | 3 μm |
| Ex. 44 | Ink Jet Aqueous Ink 3 | Self-Dispersion Pigment 3 | Liquid Composition 1 | 0% | 0% | 1.55 | 3 μm |
| Ex. 45 | Ink Jet Aqueous Ink 4 | Self-Dispersion Pigment 4 | Liquid Composition 1 | 0% | 0% | 1.25 | 4 μm |
| Ex. 46 | Ink Jet Aqueous Ink 5 | Self-Dispersion Pigment 5 | Liquid Composition 1 | 0% | 0% | 1.22 | 5 μm |
| Ex. 47 | Ink Jet Aqueous Ink 6 | Self-Dispersion Pigment 6 | Liquid Composition 1 | 0% | 24% | 1.10 | 12 μm |

TABLE 3-continued

| | | Self-dispersion pigment in ink | Liquid composition | Rate of change in average particle size | | Image density | Maximum bleeding length |
|---|---|---|---|---|---|---|---|
| | | | | 2 week | 1 month | | |
| Ex. 48 | Ink Jet Aqueous Ink 7 | Self-Dispersion Pigment 7 | Liquid Composition 1 | 0% | 0% | 1.32 | 3 μm |
| Ex. 49 | Ink Jet Aqueous Ink 8 | Self-Dispersion Pigment 8 | Liquid Composition 1 | 0% | 0% | 1.29 | 6 μm |
| Ex. 50 | Ink Jet Aqueous Ink 9 | Self-Dispersion Pigment 9 | Liquid Composition 1 | 0% | 0% | 1.22 | 9 μm |
| Ex. 51 | Ink Jet Aqueous Ink 10 | Self-Dispersion Pigment 10 | Liquid Composition 1 | 0% | 0% | 1.11 | 20 μm |
| Ex. 52 | Ink Jet Aqueous Ink 11 | Self-Dispersion Pigment 11 | Liquid Composition 1 | 0% | 0% | 1.4 | 4 μm |
| Ex. 53 | Ink Jet Aqueous Ink 12 | Self-Dispersion Pigment 12 | Liquid Composition 1 | 0% | 1% | 1.45 | 3 μm |
| Ex. 54 | Ink Jet Aqueous Ink 13 | Self-Dispersion Pigment 13 | Liquid Composition 1 | 0% | 4% | 1.45 | 3 μm |
| Ex. 55 | Ink Jet Aqueous Ink 14 | Self-Dispersion Pigment 14 | Liquid Composition 1 | 2% | 31% | 1.47 | 3 μm |
| Ex. 56 | Ink Jet Aqueous Ink 15 | Self-Dispersion Pigment 15 | Liquid Composition 1 | 0% | 2% | 1.33 | 3 μm |
| Ex. 57 | Ink Jet Aqueous Ink 16 | Self-Dispersion Pigment 16 | Liquid Composition 1 | 0% | 0% | 1.31 | 3 μm |
| Ex. 58 | Ink Jet Aqueous Ink 17 | Self-Dispersion Pigment 17 | Liquid Composition 1 | 0% | 0% | 1.42 | 3 μm |
| Ex. 59 | Ink Jet Aqueous Ink 18 | Self-Dispersion Pigment 18 | Liquid Composition 1 | 0% | 0% | 1.51 | 3 μm |
| Ex. 60 | Ink Jet Aqueous Ink 19 | Self-Dispersion Pigment 19 | Liquid Composition 1 | 0% | 0% | 1.29 | 4 μm |
| Ex. 61 | Ink Jet Aqueous Ink 20 | Self-Dispersion Pigment 20 | Liquid Composition 1 | 0% | 3% | 1.27 | 5 μm |
| Ex. 62 | Ink Jet Aqueous Ink 21 | Self-Dispersion Pigment 21 | Liquid Composition 1 | 3% | 35% | 1.20 | 10 μm |
| Ex. 63 | Ink Jet Aqueous Ink 22 | Self-Dispersion Pigment 22 | Liquid Composition 1 | 0% | 0% | 1.29 | 3 μm |
| Ex. 64 | Ink Jet Aqueous Ink 23 | Self-Dispersion Pigment 23 | Liquid Composition 1 | 0% | 0% | 1.26 | 7 μm |
| Ex. 65 | Ink Jet Aqueous Ink 24 | Self-Dispersion Pigment 24 | Liquid Composition 1 | 0% | 0% | 1.20 | 7 μm |
| Ex. 66 | Ink Jet Aqueous Ink 25 | Self-Dispersion Pigment 25 | Liquid Composition 1 | 0% | 0% | 1.12 | 19 μm |
| Ex. 67 | Ink Jet Aqueous Ink 26 | Self-Dispersion Pigment 26 | Liquid Composition 1 | 1% | 4% | 1.38 | 4 μm |
| Ex. 68 | Ink Jet Aqueous Ink 27 | Self-Dispersion Pigment 27 | Liquid Composition 1 | 0% | 8% | 1.44 | 3 μm |
| Ex. 69 | Ink Jet Aqueous Ink 28 | Self-Dispersion Pigment 28 | Liquid Composition 1 | 1% | 29% | 1.45 | 3 μm |
| Ex. 70 | Ink Jet Aqueous Ink 29 | Self-Dispersion Pigment 29 | Liquid Composition 1 | 6% | 43% | 1.48 | 3 μm |
| Ex. 71 | Ink Jet Aqueous Ink 30 | Self-Dispersion Pigment 30 | Liquid Composition 1 | 0% | 0% | 1.32 | 3 μm |
| Ex. 72 | Ink Jet Aqueous Ink 31 | Self-Dispersion Pigment 31 | Liquid Composition 1 | 0% | 3% | 1.33 | 3 μm |
| Ex. 73 | Ink Jet Aqueous Ink 32 | Self-Dispersion Pigment 32 | Liquid Composition 1 | 0% | 12% | 1.31 | 4 μm |
| Ex. 74 | Ink Jet Aqueous Ink 33 | Self-Dispersion Pigment 33 | Liquid Composition 1 | 0% | 10% | 1.31 | 3 μm |
| Ex. 75 | Ink Jet Aqueous Ink 34 | Self-Dispersion Pigment 34 | Liquid Composition 1 | 0% | 8% | 1.31 | 3 μm |
| Ex. 76 | Ink Jet Aqueous Ink 35 | Self-Dispersion Pigment 35 | Liquid Composition 1 | 0% | 0% | 1.30 | 4 μm |
| Ex. 77 | Ink Jet Aqueous Ink 36 | Self-Dispersion Pigment 36 | Liquid Composition 1 | 1% | 5% | 1.30 | 3 μm |
| Ex. 78 | Ink Jet Aqueous Ink 37 | Self-Dispersion Pigment 37 | Liquid Composition 1 | 0% | 0% | 1.32 | 3 μm |
| Ex. 79 | Ink Jet Aqueous Ink 38 | Self-Dispersion Pigment 38 | Liquid Composition 1 | 0% | 22% | 1.35 | 3 μm |
| Ex. 80 | Ink Jet Aqueous Ink 39 | Self-Dispersion Pigment 39 | Liquid Composition 1 | 0% | 0% | 1.31 | 3 μm |
| Ex. 81 | Ink Jet Aqueous Ink 40 | Self-Dispersion Pigment 40 | Liquid Composition 1 | 0% | 12% | 1.33 | 3 μm |
| Ex. 82 | Ink Jet Aqueous Ink 41 | Self-Dispersion Pigment 41 | Liquid Composition 1 | 0% | 0% | 1.31 | 3 μm |
| Comp. Ex. 5 | Ink Jet Aqueous Ink 42 | Self-Dispersion Pigment 42 | Liquid Composition 1 | 20% | 362% | 1.36 | 3 μm |
| Comp. Ex. 6 | Ink Jet Aqueous Ink 43 | Self-Dispersion Pigment 43 | Liquid Composition 1 | 11% | 208% | 1.37 | 3 μm |

TABLE 3-continued

|  |  | Self-dispersion pigment in ink | Liquid composition | Rate of change in average particle size 2 week | Rate of change in average particle size 1 month | Image density | Maximum bleeding length |
|---|---|---|---|---|---|---|---|
| Comp. Ex. 7 | Ink Jet Aqueous Ink 44 | Self-Dispersion Pigment 44 | Liquid Composition 1 | 0% | 0% | 0.82 | 42 μm |
| Comp. Ex. 8 | Ink Jet Aqueous Ink 45 | Self-Dispersion Pigment 45 | Liquid Composition 1 | 0% | 0% | 0.85 | 38 μm |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-104215, filed Apr. 22, 2009, which is hereby incorporated by reference herein in its entirety.

What is claimed is:

1. A self-dispersion pigment comprising:
 a pigment;
 an ionic group directly bonded to the pigment; and
 a nonionic molecular chain bonded to the pigment through an amide bond,
 wherein a molecular chain of the nonionic molecular chain is an alkyl ether.

2. The self-dispersion pigment according to claim 1, wherein an amount of the nonionic molecular chain to the pigment is 0.010 mmol/g or higher, a total amount of the nonionic molecular chain and the ionic group to the pigment is 0.20 mmol/g or more, and a proportion of the ionic group to the total amount is 5.0% or more.

3. The self-dispersion pigment according to claim 1, wherein the ionic group is an anionic group.

4. The self-dispersion pigment according to claim 1, wherein the ionic group is —COO(M) in which M is one of a hydrogen atom, alkali metal, ammonium and organic ammonium.

5. The self-dispersion pigment according to claim 1, wherein a weight-average molecular weight of the alkyl ether is 500 or more and 10,000 or less.

6. An ink jet aqueous ink comprising the self-dispersion pigment according to claim 1 and an aqueous medium.

7. An ink set comprising the ink jet aqueous ink according to claim 6 and a liquid composition containing a component for aggregating the self-dispersion pigment.

8. The ink set according to claim 7, wherein the ionic group is an anionic group, and the component for aggregating the self-dispersion pigment is any one of a metal salt, a pH buffering agent and a cationic polymer.

9. A process for producing a self-dispersion pigment, comprising causing a pigment to which a carboxyl group or sulfonic group is directly bonded, a condensing agent, and an amine compound to react with one another,
 wherein the self-dispersion pigment includes a nonionic molecular chain bonded to the pigment through an amide bond, and
 wherein a molecular chain of the nonionic molecular chain is an alkyl ether.

10. The production process according to claim 9, wherein the pigment to which the carboxyl group or sulfonic group is directly bonded and the condensing agent are caused to react with each other and are then reacted with the amine compound.

11. The production process according to claim 9, wherein a pigment to which a carboxyl group is directly bonded is obtained by using an oxidizing agent.

12. The production process according to claim 9, wherein the condensing agent is 4-(4,6-dimethoxy-1,3,5-triazine-2-yl)-4-methylmorpholinium chloride.

13. An ink jet recording method using the ink set according to claim 7 comprising applying the ink jet aqueous ink and the liquid composition to a recording medium so as to come into contact with each other.

14. The production process according to claim 9, wherein a weight-average molecular weight of the alkyl ether is 500 or more and 10,000 or less.

* * * * *